United States Patent
Alig

[19]

[11] Patent Number: 5,892,030

[45] Date of Patent: Apr. 6, 1999

[54] PROCESS FOR PRODUCING 5,6-DIHYDRO-1,3-OXAZINES

[75] Inventor: Bernd Alig, Königswinter, Germany

[73] Assignee: Bayer Aktiengesellschaft, Leverkusen, Germany

[21] Appl. No.: 930,051

[22] PCT Filed: May 9, 1996

[86] PCT No.: PCT/EP96/01954

§ 371 Date: Nov. 14, 1997

§ 102(e) Date: Nov. 14, 1997

[87] PCT Pub. No.: WO96/37484

PCT Pub. Date: Nov. 28, 1996

[30] Foreign Application Priority Data

May 22, 1995 [DE] Germany .................. 195 18 681.8

[51] Int. Cl.$^6$ .................. C07D 265/08; C07D 295/125
[52] U.S. Cl. .................................... 544/88; 544/96
[58] Field of Search ............... 544/88, 96; 514/228.8

[56] References Cited

U.S. PATENT DOCUMENTS 5,538,967  7/1996  Long et al. ....................... 514/226.8

FOREIGN PATENT DOCUMENTS

| | | |
|---|---|---|
| 394850 | 10/1990 | European Pat. Off. . |
| 1545671 | 8/1969 | Germany . |
| 1670475 | 1/1971 | Germany . |
| 2049160 | 4/1972 | Germany . |
| 93/2296 | 11/1993 | WIPO . |
| WO 94/14783 | 7/1994 | WIPO ....................... 544/88 |

OTHER PUBLICATIONS

Schmidt et al., Agnew. Chem., 77, 5, 1965, 218 pp.
W. Seeliger et al., Liebigs Annalen, 697, 1966, 171pp.
Schmidt et al., Agnew. Chem., 81, 15, 1969, 576pp.
Schmidt et al., Chem. Ber. 103, 1970, 3242pp.
Giordano et al., Synthesis, 1971, 92pp.
Giordano et al., Synthesis, 1972, 34pp.
Giordano et al., JCS Perkin Trans. I, 1973, 771pp.
Foglia et al., J. of the Am. Oil Chemists Soc., 50, 1973, p. 9/10.
Giordano et al., Gazz. Chim. Ital., 104, 1974, 181pp.
Zaugg et al., Synthesis, 1984, 85pp.
Zaugg et al., Synthesis, 1984, 1181pp.
Hans Bundgaard et al., Int. J. of Pharmaceuttics. 22, 1984, 44pp.
Katritzky et al., Tetr. 49, 19, 1993, 3907pp.

*Primary Examiner*—Richard L. Raymond
*Attorney, Agent, or Firm*—Sprung Kramer Schaefer & Briscoe

[57] ABSTRACT

There has been found a new process for the preparation of 5,6-dihydro-1,3-oxazines, some of which are known, of the formula (I)

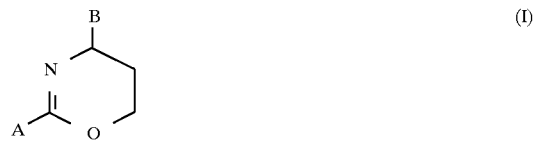

(I)

in which

A represents substituted phenyl, or represents in each case optionally substituted naphthyl, pyridyl, thienyl or pyrazolyl, and B represents hydrogen, alkyl, alkoxyalkyl, alkylthioalkyl, halogenoalkyl, alkenyl, optionally substituted cycloalkyl, or in each case optionally substituted phenyl, phenylalkyl, phenylalkenyl, phenoxyalkyl, phenylthioalkyl, pyridyl or 2- or 3-pyrrolyl by reacting amide derivatives of the formula (II)

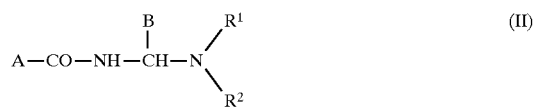

(II)

with ethylene in the presence of hydrogen chloride gas and of a catalyst.

The new 5,6-dihydro-1,3-oxazines can be used for combatting animal pests.

1 Claim, No Drawings

PROCESS FOR PRODUCING 5,6-DIHYDRO-1,3-OXAZINES

This application is a 371 of PCT/EP96/01954, filed May 9, 1996.

The invention relates to a new process for the preparation of 5,6-dihydro-1,3-oxazines, some of which are new, to new 5,6-dihydro-1,3-oxazines, and to new intermediates for their preparation and their use for combating animal pests.

It is known that 5,6-dihydro-1,3-oxazines are obtained when aminoalcohols of the formula (A) are reacted with carboxylic acids of the formula (B) in the presence of a dehydrating agent in accordance with the following equation:

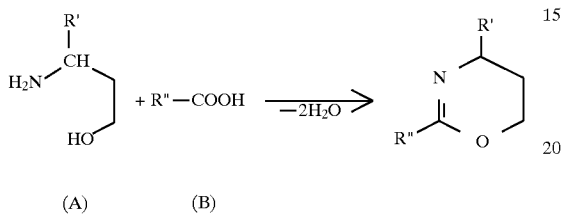

(cf., in this context, EP-A 0 635 500 and WO-A 94/14783).

Furthermore, it is known that 5,6-dihydro-1,3-oxazines are obtained when amino-alcohols of the formula (A) are first reacted with acid chlorides of the formula (C) and the resulting amidoalcohols of the formula (D) are subsequently cyclized with dehydrating agent in accordance with the following equation:

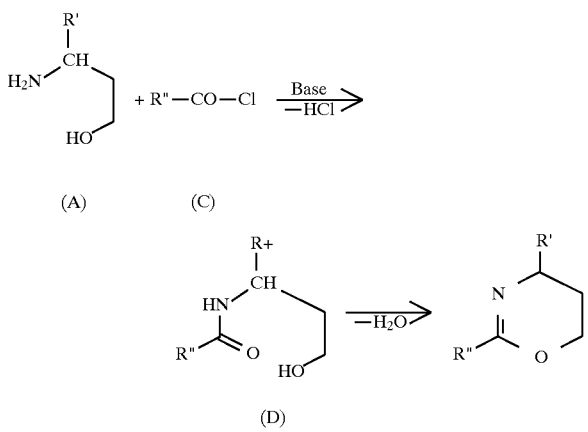

(cf., in this context, EP-A 0 635 500 and WO-A 94/14783).

Furthermore, it is known that 5,6-dihydro-1,3-oxazines are obtained when amino-alcohols of the formula (E) are reacted with nitriles of the formula (F) in the presence of rhodium complexes, if appropriate with an addition of diphosphines, in accordance with the following equation:

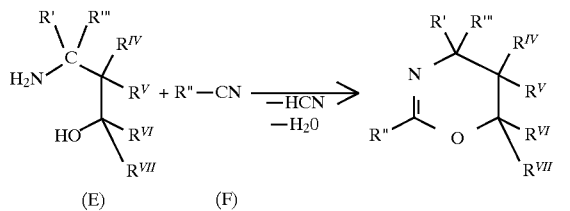

(cf., in this context, JP-A 06 298 746).

However, the product yields which can be obtained in these known synthetic methods are not satisfactory, in particular with a view to the overall process, i.e. including the preparation of the aminoalcohols of the formulae (A) and (E) required as starting substances: The aminoalcohols can only be obtained in unsatisfactory yields via a plurality of steps and using expensive precursors and reducing agents, additional technical problems occurring due to substantial amounts of reducing agents and solvents and due to the fact that some processes have to be carried out under inert gas.

It has now been found that 5,6-dihydro-1,3-oxazines of the formula (I)

in which
A represents substituted phenyl, or represents in each case optionally substituted naphthyl, pyridyl, thienyl or pyrazolyl, and
B represents hydrogen, alkyl, alkoxyalkyl, alkylthioalkyl, halogenoalkyl, alkenyl, optionally substituted cycloalkyl, or in each case optionally substituted phenyl, phenylalkyl, phenylalkenyl, phenoxyalkyl, phenylthioalkyl, pyridyl or 2- or 3-pyrrolyl
are obtained when amide derivatives of the formula (II)

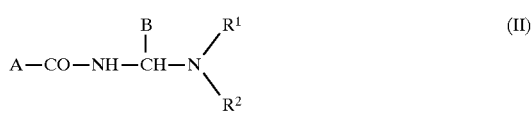

in which
A and B have the abovementioned meanings and
$R^1$ and $R^2$ are identical or different and in each case represent alkyl, or together with the N atom to which they are bonded represent an optionally substituted heterocycle
are reacted with ethylene in the presence of hydrogen chloride gas and of a catalyst, if appropriate in the presence of a diluent.

Surprisingly, the process according to the invention allows 5,6-dihydro-1,3-oxazines of the formula (I) to be obtained in good yields and in high purity, even though no noticeable reaction was to be expected due to the low reactivity of ethylene.

Thus, the reaction according to the invention has the advantage of being easier to carry out while simultaneously improving the yield, in particular with a view to the overall process, i.e. taking into consideration the preparation of the precursors (cf. also the preparation examples).

Formula (I) provides a general definition of the compounds to be prepared according to the invention. Preferred substituents or ranges of the radicals listed in the formulae mentioned hereinabove and hereinbelow are illustrated in the following text.

A preferably represents phenyl which is monosubstituted to pentasubstituted by identical or different substituents from the series consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro, cyano or by phenyl which is optionally monosubstituted to pentasubstituted by identical or different substituents from the series consisting of halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, or represents naphthyl which is optionally monosubstituted to trisubstituted by identical or different substituents from the series consisting of halogen, $C_1$–$C_6$-alkyl, $C_1$–$C_6$-alkoxy and $C_1$–$C_6$-halogenoalkoxy, or represents pyridyl which is optionally monosubstituted to trisubstituted by identical or different substituents from the series consisting of halogen, $C_1$–$C_6$-alkyl, $C_1$–$C_6$-alkoxy, $C_1$–$C_6$-halogenoalkyl, $C_1$–$C_6$-halogenoalkoxy and cyano, or represents thienyl which is optionally monosubstituted to trisubstituted by identical or different substituents from the series consisting of halogen and $C_1$–$C_6$-alkyl, or represents pyrazolyl which is optionally monosubstituted to trisubstituted by identical or different substituents from the series consisting of halogen and $C_1$–$C_3$-alkyl.

B preferably represents hydrogen, $C_1$–$C_6$-alkyl, $C_1$–$C_6$-alkoxy-$C_1$–$C_6$-alkyl, $C_1$–$C_6$-alkylthio-$C_1$–$C_6$-alkyl, $C_1$–$C_6$-halogenoalkyl and $C_2$–$C_6$-alkenyl, or represents $C_3$–$C_7$-cycloalkyl which is optionally monosubstituted to pentasubstituted by identical or different substituents from the series consisting of halogen, $C_1$–$C_6$-alkyl, $C_1$–$C_6$-alkoxy, $C_1$–$C_6$-halogenoalkyl and $C_1$–$C_6$-halogenoalkoxy, or represents pyridyl which is optionally monosubstituted to trisubstituted by identical or different substituents from the series consisting of halogen, $C_1$–$C_6$-alkyl, $C_1$–$C_6$-alkoxy, $C_1$–$C_6$-halogenoalkyl, $C_1$–$C_6$-halogenoalkoxy and cyano, or represents α-pyrrolyl or β-pyrrolyl, each of which is optionally monosubstituted or disubstituted by identical or different substituents from the series consisting of halogen and $C_1$–$C_4$-alkyl, or represents phenyl which is substituted by hydroxyl, CHO, cyano, carboxyl, poly-$C_1$–$C_8$-alkoxy-$C_1$–$C_8$-alkyl or $C_1$–$C_8$-alkoxycarbonyl or represents phenyl, benzyl, pheneth-1-yl, pheneth-2-yl, phenoxymethyl, phenylthiomethyl, phenylthioeth-1-yl, phenoxyeth-1-yl, phenoxyeth-2-yl or styryl, each of which is optionally monosubstituted to pentasubstituted in the phenyl ring by identical or different substituents, suitable substituents in each case being
halogen
$C_1$–$C_{18}$-alkyl,
$C_1$–$C_8$-alkoxy-$C_1$–$C_8$-alkyl,
$C_1$–$C_8$-halogenoalkoxy,
$C_1$–$C_4$-halogenoalkyl,
$C_1$–$C_{18}$-alkoxy which is optionally interrupted by a further 1 to 3 oxygen atoms,
$C_1$–$C_{18}$-alkylthio,
$C_1$–$C_8$-halogenoalkylthio,
tri-($C_1$–$C_8$)-alkylsilyl,
phenyl-di-($C_1$–$C_8$)-alkylsilyl,
3,4-difluoromethylenedioxo,
3,4-tetrafluoroethylenedioxo,
a fused benzo group,
a fused $C_3$–$C_4$-alkanediyl group,
benzyliminooxymethyl which is optionally substituted by halogen, $C_1$–$C_4$-alkyl or $C_3$–$C_6$-cycloalkyl,
cyclohexyl or cyclohexyloxy, each of which is optionally substituted by $C_1$–$C_6$-alkyl, $C_1$–$C_6$-alkoxy, cyclohexyl or phenyl,
pyridyloxy which is optionally monosubstituted or disubstituted by identical or different substituents from the series consisting of halogen, $C_1$–$C_4$-alkyl and $C_1$–$C_4$-halogenoalkyl,
phenyl, phenyl-$C_1$–$C_6$-alkyl, phenoxy, phenylthio, phenyl-$C_1$–$C_6$-alkoxy or benzylthio, each of which is optionally monosubstituted to pentasubstituted by identical or different substituents from the series consisting of halogen, $C_1$–$C_{12}$-alkyl, $C_1$–$C_4$-halogenoalkyl, $C_1$–$C_{12}$-alkoxy, $C_1$–$C_6$-halogenoalkoxy, $C_1$–$C_6$-alkoxy-$C_1$–$C_6$-alkyl, $C_1$–$C_6$-alkoxy-ethyleneoxy, $C_1$–$C_6$-alkylthio and $C_1$–$C_6$-halogenoalkylthio.

A particularly preferably represents phenyl which is monosubstituted to tetrasubstituted by identical or different substituents from the series consisting of fluorine, chlorine, bromine, $C_1$–$C_3$-alkyl, $C_1$–$C_3$-alkoxy, $C_1$–$C_3$-alkylthio, by $C_1$–$C_2$-alkyl which is monosubstituted to pentasubstituted by identical or different substituents from the series consisting of fluorine and chlorine, by $C_1$–$C_4$-alkoxy which is monosubstituted to pentasubstituted by identical or different substituents from the series consisting of fluorine and chlorine, by $SCF_3$, $SCHF_2$, nitro, cyano, or by phenyl which is optionally monosubstituted to tetrasubstituted by identical or different substituents from the series consisting of fluorine, chlorine, bromine, $C_1$–$C_4$-alkyl, $C_1$–$C_4$-alkoxy, $C_1$–$C_4$-alkylthio, $C_1$–$C_2$-alkyl which is monosubstituted to pentasubstituted by identical or different substituents from the series consisting of fluorine and chlorine, by $C_1$–$C_4$-alkoxy which is monosubstituted to pentasubstituted by identical or different substituents from the series consisting of fluorine and chlorine, or by $SCF_3$ or $SCHF_2$, or represents naphthyl which is optionally monosubstituted to trisubstituted by identical or different substituents from the series consisting of fluorine, chlorine, $C_1$–$C_6$-alkyl, $C_1$–$C_6$-alkoxy and $C_1$–$C_6$-alkoxy which is monosubstituted to trisubstituted by identical or different substituents from the series consisting of fluorine and chlorine, or represents pyridyl which is optionally monosubstituted or disubstituted by identical or different substituents from the series consisting of fluorine, chlorine, $C_1$–$C_3$-alkyl, $C_1$–$C_3$-alkoxy, $CF_3$, $OCF_3$ and cyano, or represents thienyl which is optionally monosubstituted or disubstituted by identical or different substituents from the series consisting of chlorine, bromine, methyl and ethyl, or represents pyrazolyl which is optionally monosubstituted to trisubstituted by identical or different substituents from the series consisting of fluorine, chlorine, bromine and $C_1$–$C_3$-alkyl.

B particularly preferably represents hydrogen, $C_1$–$C_4$-alkyl, $C_1$–$C_4$-alkoxy-$C_1$–$C_4$-alkyl, $C_1$–$C_4$-alkylthio-$C_1$–$C_4$-alkyl, $C_1$–$C_4$-halogenoalkyl or $C_2$–$C_6$-alkenyl, or represents cyclopropyl, cyclopentyl or cyclohexyl, each of which is optionally monosubstituted to trisubstituted by identical or different substituents from the series consisting of fluorine, chlorine, bromine, $C_1$–$C_3$-alkyl, $C_1$–$C_3$-alkoxy, $CF_3$ and $OCF_3$, or represents pyridyl which is optionally monosubstituted or disubstituted by identical or different substituents from the series consisting of fluorine, chlorine, $C_1$–$C_3$-alkyl, $C_1$–$C_3$-alkoxy, $CF_3$, $OCF_3$ and cyano, or represents α-pyrrolyl or β-pyrrolyl, each of which is optionally monosubstituted or disubstituted by identical or different substituents from the series consisting of fluorine, chlorine and $C_1$–$C_3$-alkyl, or represents phenyl which is substituted by CHO, cyano, hydroxyl, carboxyl, poly-$C_1$–$C_8$-alkoxy-$C_1$–$C_6$-alkyl and $C_1$–$C_8$-alkoxycarbonyl or, or represents phenyl, benzyl, pheneth-1-yl, pheneth-2-yl, phenoxymethyl, phenylthiomethyl, phenylthioeth-1-yl, phenoxyeth-1-yl, phenoxyeth-2-yl or styryl, each of which is optionally monosubstituted to tetrasubstituted in the phenyl ring by identical or different substituents, suitable substituents in each case being fluorine, chlorine, bromine,
$C_1$–$C_{18}$-alkyl,
$C_1$–$C_6$-alkoxy-$C_1$–$C_8$-alkyl,
$C_1$–$C_8$-alkoxy which is monosubstituted to hexasubstituted by identical or different substituents from the series consisting of fluorine and chlorine,
$C_1$–$C_2$-alkyl which is monosubstituted to pentasubstituted by identical or different substituents from the series consisting of fluorine and chlorine,
$C_1$–$C_{18}$-alkoxy or —(O$C_2H_4$)$_{1-3}$—O—$C_1$–$C_6$-alkyl,
$C_1$–$C_{15}$-alkylthio,
$C_1$–$C_8$-alkylthio, which is monosubstituted to hexasubstituted by identical or different substituents from the series consisting of fluorine and chlorine,
tri-($C_1$–$C_6$)-alkylsilyl,
phenyl-di-($C_1$–$C_6$)-alkylsilyl,
3,4-difluoromethylenedioxo,
3,4-tetrafluoroethylenedioxo,
a fused benzo group,
a fused $C_4$-alkanediyl group,
the groups

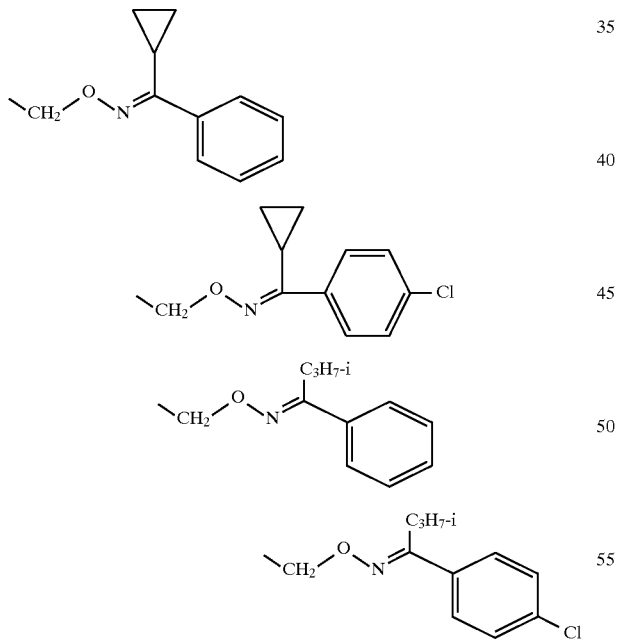

cyclohexyl or cyclohexyloxy, each of which is optionally substituted by $C_1$–$C_4$-alkyl, $C_1$–$C_4$-alkoxy, cyclohexyl or phenyl, pyridyloxy which is optionally monosubstituted or disubstituted by identical or different substituents from the series consisting of fluorine, chlorine and $CF_3$, phenyl, phenyl-$C_1$–$C_6$-alkyl, phenoxy, phenylthio, phenyl-$C_1$–$C_6$-alkoxy or benzylthio, each of which is optionally monosubstituted to tetrasubstituted by identical or different substituents from the series consisting of fluorine, chlorine, bromine, $C_1$–$C_{12}$-alkyl, $C_1$–$C_4$-alkyl which is monosubstituted to hexasubstituted by identical or different substituents from the series consisting of fluorine and chlorine, or by $C_1$–$C_{12}$-alkoxy, $C_1$–$C_4$-alkoxy, which is monosubstituted to hexasubstituted by identical or different substituents from the series consisting of fluorine and chlorine, or by $C_1$–$C_4$-alkoxy-$C_1$–$C_4$-alkyl, $C_1$–$C_4$-alkoxyethyleneoxy, $C_1$–$C_4$-alkylthio or $C_1$–$C_4$-alkylthio which is monosubstituted to hexasubstituted by identical or different substituents from the series consisting of fluorine and chlorine.

A very particularly preferably represents phenyl which is monosubstituted to trisubstituted by identical or different substituents from the series consisting of fluorine, chlorine, bromine, $C_1$–$C_3$-alkyl, $C_1$–$C_3$-alkoxy, $C_1$–$C_3$-alkylthio, $C_1$–$C_2$-alkyl which is monosubstituted to pentasubstituted by identical or different substituents from the series consisting of fluorine and chlorine, by $C_1$–$C_4$-alkoxy which is monosubstituted to pentasubstituted by identical or different substituents from the series consisting of fluorine and chlorine, by $SCF_3$, $SCHF_2$, nitro, cyano, or by phenyl which is optionally monosubstituted to tetrasubstituted by identical or different substituents from the series consisting of fluorine, chlorine, bromine, $C_1$–$C_3$-alkyl, $C_1$–$C_3$-alkoxy, $C_1$–$C_3$-alkylthio, $C_1$–$C_2$-alkyl which is monosubstituted to pentasubstituted by identical or different substituents from the series consisting of fluorine and chlorine, by $C_1$–$C_4$-alkoxy which is monosubstituted to pentasubstituted by identical or different substituents from the series consisting of fluorine and chlorine, or by $SCF_3$ or $SCHF_2$.

B very particularly preferably represents hydrogen, $C_1$–$C_4$-alkyl, $C_1$–$C_2$-alkoxy-$C_1$–$C_4$-alkyl, $C_1$–$C_2$-alkylthio-$C_1$–$C_4$-alkyl, $C_1$–$C_2$-halogenoalkyl or $C_2$–$C_4$-alkenyl, or represents cyclopropyl, cyclopentyl or cyclohexyl, each of which is optionally monosubstituted to trisubstituted by identical or different substituents from the series consisting of fluorine, chlorine, $CH_3$, $C_2H_5$, $OCH_3$, $CF_3$ or $OCF_3$, or represents pyridyl which is optionally monosubstituted or disubstituted by identical or different substituents from the series consisting of fluorine, chlorine, $CH_3$, $C_2H_5$, $OCH_3$, $CF_3$, $OCF_3$ and cyano, or represents α-pyrrolyl or β-pyrrolyl, each of which is optionally monosubstituted or disubstituted by identical or different substituents from the series consisting of fluorine, chlorine $CH_3$ and $C_2H_5$, or represents phenyl which is substituted by CHO, hydroxyl, cyano, carboxyl, di-$C_1$–$C_6$-alkoxy-$C_1$–$C_4$-alkyl or $C_1$–$C_6$-alkoxycarbonyl, or represents phenyl, benzyl, pheneth-1-yl, pheneth-2-yl, phenoxymethyl, phenylthiomethyl, phenylthioeth-1-yl, phenoxyeth-1-yl, phenoxyeth-2-yl or styryl, each of which is optionally monosubstituted to trisubstituted in the phenyl ring by identical or different substituents, suitable substituents in each case being fluorine, chlorine, bromine,
$C_1$–$C_{18}$-alkyl,
$C_1$–$C_6$-alkoxy-$C_1$–$C_8$-alkyl,
$C_1$–$C_8$-alkoxy which is monosubstituted to hexasubstituted by identical or different substituents from the series consisting of fluorine and chlorine, C₁–C₂-alkyl which is monosubstituted to pentasubstituted by identical or different substituents from the series consisting of fluorine and chlorine,
C₁–C₁₈-alkoxy or —(OC₂H₄)₁₋₃—O—C₁–C₆-alkyl,
C₁–C₁₅-alkylthio,
C₁–C₈-alkylthio, which is monosubstituted to hexasubstituted by identical or different substituents from the series consisting of fluorine and chlorine,
tri-(C₁–C₆)-alkylsilyl,
phenyl-di-(C₁–C₆)-alkylsilyl,
3,4-difluoromethylenedioxo,
3,4-tetrafluoroethylenedioxo,
a fused benzo group,
a fused C₄-alkanediyl group,
the groups

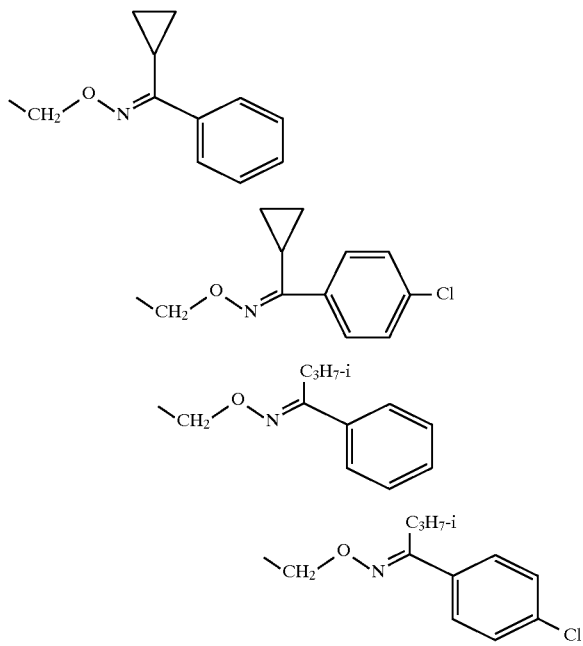

cyclohexyl or cyclohexyloxy, each of which is optionally substituted by C₁–C₄-alkyl, C₁–C₄-alkoxy, cyclohexyl or phenyl,
pyridyloxy which is optionally monosubstituted or disubstituted by identical or different substituents from the series consisting of fluorine, chlorine and CF₃,
phenyl, phenyl-C₁–C₆-alkyl, phenoxy, phenylthio, phenyl-C₁–C₆-alkyloxy or benzylthio, each of which is optionally monosubstituted to tetrasubstituted by identical or different substituents from the series consisting of fluorine, chlorine, bromine, C₁–C₁₂-alkyl, C₁–C₄-alkyl which is monosubstituted to hexasubstituted by fluorine or chlorine, or C₁–C₁₂-alkoxy, C₁–C₄-alkoxy which is monosubstituted to hexasubstituted by identical or different substituents from the series consisting of fluorine and chlorine, or by C₁–C₄-alkoxy-C₁–C₄-alkyl, C₁–C₄-alkoxy-ethyleneoxy, C₁–C₄-alkylthio or C₁–C₄-alkylthio which is monosubstituted to hexasubstituted by identical or different substituents from the series consisting of fluorine and chlorine.

Preferred compounds which can be prepared according to the invention are substances of the formula (Ia)

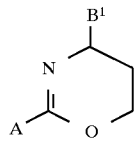

(Ia)

in which

A has the abovementioned general, preferred, particularly preferred and very particularly preferred meanings and B¹ represents phenyl which is monosubstituted to pentasubstituted by identical or different substituents, suitable substituents being those which have been mentioned above under B as being preferred, particularly preferred and very particularly preferred for the phenyl radical.

A particularly preferred group of substances which can be prepared according to the invention are compounds of the formula (I)

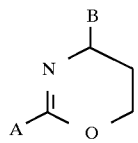

(I)

in which

A represents phenyl which is monosubstituted or disubstituted by identical or different substituents from the series consisting of fluorine and chlorine and B represents phenyl which is monosubstituted to trisubstituted by identical or different substituents from the series consisting of fluorine, chlorine, bromine, C₁–C₈-alkyl, C₁–C₈-alkoxy, C₁–C₄-halogenoalkyl, C₁–C₄-halogenoalkoxy, C₁–C₈-alkylthio and C₃–C₆-cycloalkyl or represents phenyl which is monosubstituted by phenyl, phenyl-C₁–C₃-alkyl, phenyloxy or benzyloxy, each of which is optionally monosubstituted or disubstituted in the phenyl moiety by identical or different substituents from the series consisting of fluorine, chlorine, bromine, C₁–C₆-alkyl, C₁–C₆-alkoxy, C₁–C₄-halogenoalkyl and C₁–C₄-halogenoalkoxy, or represents pyridyl or 2- or 3-pyrrolyl, each of which is optionally monosubstituted or disubstituted by identical or different substituents from the series consisting of fluorine, chlorine, methyl, ethyl and trifluoromethyl, or represents phenyl which is substituted by CHO, hydroxyl, cyano, carboxyl, di-C₁–C₆-alkoxy-C₁–C₄-alkyl or C₁–C₆-alkoxycarbonyl.

If, for example, N-[morpholin-4-yl(4-tert-butylphenyl)-methyl]-2,6-difluorobenzamide and ethylene are used as starting substances in the presence of HCl gas and titanium tetrachloride as the catalyst, the course of the reaction of the process according to the invention can be represented by the following equation:

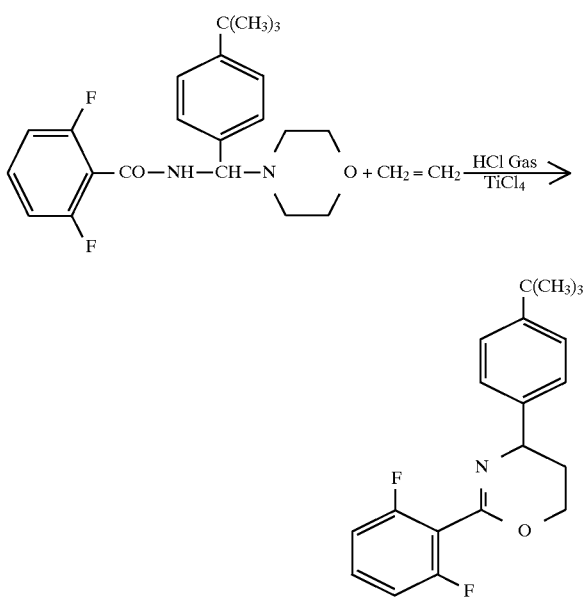

Formula (II) provides a general definition of the amide derivative to be used as starting substances in the process according to the invention. In Formula (II), A and B preferably, or in particular, have those meanings which have already been mentioned above in connection with the description of the compounds of the formula (I) which can be prepared according to the invention as being preferred, particularly preferred or very particularly preferred for A and B.

$R^1$ and $R^2$ are identical or different and preferably represent $C_1-C_4$-alkyl, in particular methyl, ethyl or n- or i-propyl, or together with the N atom to which they are bonded preferably represent a 5- or 6-membered heterocycle which is optionally monosubstituted to pentasubstituted, preferably monosubstituted or disubstituted, by identical or different substituents and which can optionally contain one or two further hetero atoms, preferably one further hetero atom, such as O, S or NR, substituents which may be mentioned being, in particular, $C_1-C_4$-alkyl and $C_1-C_4$-alkoxy, and R representing alkyl, preferably $C_1-C_4$-alkyl, or optionally substituted aryl, in particular phenyl which is optionally monosubstituted or disubstituted by identical or different substituents, substituents which may preferably be mentioned being: halogen, $C_1-C_4$-alkyl, $C_1-C_4$-halogenoalkyl, $C_1-C_4$-alkoxy, $C_1-C_4$-halogenoalkoxy, $C_1-C_4$-alkylthio and $C_1-C_4$-halogenoalkylthio.

Some amide derivatives of the formula (II) in which B represents hydrogen are already known (cf., for example, Liebigs Annalen 343, 207 (1905) and Bull. Soc. Chim. France 1979, II, 409–414).

New and also subject-matter of the present application are amide derivatives of the formula (IIa)

in which

A, $R^1$ and $R^2$ have the abovementioned meanings and $B^2$ has the meaning given above for B, with the exception of hydrogen.

The amide derivatives of the formula (IIa) are obtained, for example, by reacting amides of the formula (III)

$$A-CO-NH_2 \quad (III)$$

in which

A has the abovementioned meaning
with aldehydes of the formula (IV)

$$B^2-CHO \quad (IV)$$

in which $B^2$ has the abovementioned meaning
and with amines of the formula (V)

in which $R^1$ and $R^2$ have the abovementioned meanings,
if appropriate in the presence of a diluent.

If, for example, 2,6-difluorobenzamide, 4-tert-butylbenzaldehyde and morpholine are used as starting substances, the course of the reaction in the process for the preparation of the amide derivatives of the formula (II) can be outlined by the following equation:

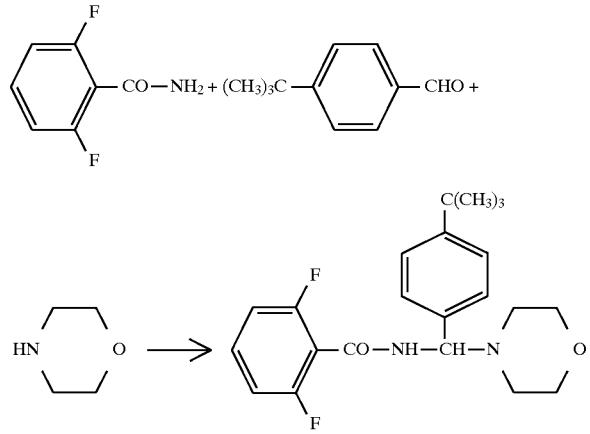

The amides of the formula (III), aldehydes of the formula (IV) and secondary amines of the formula (V) required as starting substances for the preparation of the amide derivatives of the formula (II) are generally known or can be obtained in the generally known manner.

Suitable diluents for carrying out the process for the preparation of the amide derivatives of the formula (II) are all inert organic solvents which are customary for such reactions. The following can preferably be used: alcohols, such as methanol or ethanol; esters, such as methyl acetate or ethyl acetate; ethers, such as diethyl ether, methyl tert-butyl ether, ethylene glycol dimethyl ether, tetrahydrofuran or dioxane, furthermore nitriles, such as acetonitrile; moreover optionally halogenated aliphatic, cycloaliphatic or aromatic hydrocarbons, such as methylene chloride, chloroform, carbon tetrachloride, hexane, cyclohexane, benzene, toluene, xylene or chlorobenzene; and also sulphoxides, such as dimethyl sulphoxide.

When carrying out the process for the preparation of the amide derivatives of the formula (II), the reaction temperatures can be varied within a substantial range. In general, the process is carried out at temperatures between 0° and 120° C., preferably between 10° and 100° C.

When carrying out the process for the preparation of the amide derivatives of the formula (II), 1.0 to 1.5 mol, preferably 1.0 to 1.2 mol, of aldehyde of the formula (IV) and 1.0 to 2.0 mol, preferably 1.0 to 1.2 mol, of secondary amine of the formula (V) are generally employed per mol of amide of the formula (III).

The reaction is carried out and the reaction products are worked up and isolated by generally customary methods.

If appropriate, the amide derivatives of the formula (II) can also be reacted directly, i.e. without isolation, with ethylene by the process according to the invention to give the end products of the formula (I) (cf. also the preparation examples).

The new amide derivatives of the formula (IIa) also display good biological action when used for combating animal pests.

The process according to the invention for the preparation of the compounds of the formula (I) is carried out in the presence of hydrogen chloride gas and a catalyst. Suitable catalysts are Lewis acids, preferably transition-metal halides, in particular titanium tetrachloride, tin tetrachloride and zinc dichloride.

The process according to the invention is preferably carried out in the presence of a diluent.

Suitable diluents are customary organic solvents, for example optionally halogenated aliphatic, cycloaliphatic or aromatic hydrocarbons. These include, for example, chlorobenzene, dichlorobenzene, petroleum ether, hexane, cyclohexane, dichloromethane, chloroform and tetrachloromethane.

When carrying out the process according to the invention, reaction temperatures can be varied within a substantial range. In general, the process is carried out at temperatures between −120° C. and +120° C., preferably at temperatures between 10° C. and 100° C.

At this temperature, the process is preferably carried out in a sealed vessel (autoclave) under the inherent pressure of the reaction mixture which is established. However, it is also possible to pass the ethylene through the reaction mixture under atmospheric pressure, unconsumed ethylene optionally being recirculated.

A further possibility is to condense in the ethylene at low temperatures (approximately −110° C.) and to carry out the reaction at this temperature.

To carry out the process according to the invention, between 1 and 5 mol, preferably between 1 and 3 mol, of ethylene and in each case between 1 and 5 mol, preferably between 1 and 4 mol, of hydrogen chloride gas and of catalyst are generally employed per mol of amide derivative of the formula (II).

Working-up can be carried out in the customary manner; preferably, the reaction mixture is rendered alkaline at temperatures between 0° C. and 10° C., with cooling, and the end product is isolated in the generally customary manner.

The 5,6-dihydro-1,3-oxazines of the formula (I) to be prepared by the process according to the invention are known in most cases (cf. for example, EP-A 0 635 500 and WO-A 94/14783) and are employed for combating animal pests.

New and also subject-matter of the invention are compounds of the formula (Ib)

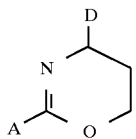

in which

A has the abovementioned meaning and

D represents in each case optionally substituted 2- or 3-pyrrolyl, or phenyl which is substituted by CHO, cyano, carboxyl, polyalkoxyalkyl or alkoxycarbonyl.

Depending on the nature of the substituents, the compounds of the formula (Ib) can also be present as geometric and/or optical isomers or variously composed isomer mixtures. The invention relates to the pure isomers and to the isomer mixtures.

Furthermore, it has been found that the compounds of the formula (Ib) can be prepared by the process according to the invention described above.

Finally, it has been found that the new compounds of the formula (Ib) are highly suitable for combating animal pests, in particular arthropods and nematodes.

Surprisingly, compounds of the formula (Ib) according to the invention display a considerably better activity against animal pests than those compounds which are most similar constitutionally.

Formula (Ib) provides a general definition of the compounds according to the invention.

Preferred substituents or ranges of the radicals mentioned in the formulae given hereinabove and hereinbelow are illustrated in the following text.

A preferably represents phenyl which is monosubstituted to pentasubstituted by identical or different substituents from the series consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro, cyano and phenyl which is optionally monosubstituted to pentasubstituted by identical or different substituents from the series consisting of halogen $C_1$–$C_6$-alkyl, $C_1$–$C_6$-halogenoalkoxy, $C_1$–$C_6$-alkoxy, $C_1$–$C_6$-halogenoalkoxy, $C_1$–$C_6$-alkylthio and $C_1$–$C_6$-halogenoalkylthio, or represents naphthyl which is optionally monosubstituted to trisubstituted by identical or different substituents, substituents which may be mentioned being halogen, $C_1$–$C_6$-alkyl, $C_1$–$C_6$-alkoxy and $C_1$–$C_6$-halogenoalkoxy, or represents pyridyl which is optionally monosubstituted to trisubstituted by identical or different substituents, substituents which may be mentioned being halogen, $C_1$–$C_6$-alkyl, $C_1$–$C_6$-alkoxy, $C_1$–$C_6$-halogenoalkyl, $C_1$–$C_6$-halogenoalkoxy and cyano, or represents thienyl which is optionally monosubstituted to trisubstituted by identical or different substituents, substituents which may be mentioned being halogen and $C_1$–$C_6$-alkyl, or represents pyrazolyl which is optionally monosubstituted to trisubstituted by identical or different substituents, substituents which may be mentioned being halogen or $C_1$–$C_3$-alkyl.

D preferably represents 2-pyrrolyl or 3-pyrrolyl, each of which is optionally monosubstituted or disubstituted by identical or different substituents from the series consisting of halogen and $C_1$–$C_4$-alkyl, or represents phenyl which is substituted by CHO, cyano, carboxyl, poly-$C_1$–$C_8$-alkoxy-$C_1$–$C_8$-alkyl or $C_1$–$C_8$-alkoxycarbonyl.

A particularly preferably represents phenyl which is monosubstituted to tetrasubstituted by identical or different substituents from the series consisting of fluorine, chlorine, bromine, $C_1$–$C_3$-alkyl, $C_1$–$C_3$-alkoxy, $C_1$–$C_3$-alkylthio, $C_1$–$C_2$-alkyl which is monosubstituted to pentasubstituted by identical or different substituents from the series consisting of fluorine and chlorine, $C_1$–$C_4$-alkoxy which is monosubstituted to pentasubstituted by identical or different substituents from the series consisting of fluorine and chlorine, $SCF_3$, $SCHF_2$, nitro, cyano, and phenyl which is optionally monosubstituted to tetrasubstituted by identical or different substituents from the series consisting of fluorine, chlorine, bromine, $C_1$–$C_4$-alkyl, $C_1$–$C_4$-alkoxy, $C_1$–$C_4$-alkylthio, $C_1$–$C_2$-alkyl which is monosubstituted to pentasubstituted by identical or different substituents from the series consisting of fluorine and chlorine, $C_1$–$C_4$-alkoxy which is monosubstituted to pentasubstituted by identical or different substituents from the series consisting of fluorine and chlorine, $SCF_3$ and $SCHF_2$, or represents naphthyl which is optionally monosubstituted to trisubstituted by identical or different substituents, substituents which may be mentioned being fluorine, chlorine, $C_1$–$C_6$-alkyl, $C_1$–$C_6$-alkoxy and $C_1$–$C_6$-alkoxy which is monosubstituted to trisubstituted by identical or different substituents from the series consisting of fluorine and chlorine, or represents pyridyl which is optionally monosubstituted or disubstituted by identical or different substituents, suitable substituents being fluorine, chlorine, $C_1$–$C_3$-alkyl, $C_1$–$C_3$-alkoxy, $CF_3$, $OCF_3$ and cyano, or represents thienyl which is optionally monosubstituted or disubstituted by identical or different substituents, substituents which may be mentioned being chlorine, bromine, methyl or ethyl, or represents pyrazolyl which is optionally monosubstituted to trisubstituted by identical or different substituents, substituents which may be mentioned being fluorine, chlorine, bromine and $C_1$–$C_3$-alkyl.

D particularly preferably represents 2-pyrrolyl or 3-pyrrolyl, each of which is optionally monosubstituted or disubstituted by identical or different substituents from the series consisting of fluorine, chlorine and $C_1$–$C_3$-alkyl, or represents phenyl which is substituted by CHO, cyano, carboxyl, poly-$C_1$–$C_1$-alkoxy-$C_1$–$C_6$-alkyl or $C_1$–$C_8$-alkoxycarbonyl.

A particularly preferably represents phenyl which is monosubstituted to trisubstituted by identical or different substituents from the series consisting of fluorine, chlorine, bromine, $C_1$–$C_3$-alkyl, $C_1$–$C_3$-alkoxy, $C_1$–$C_3$-alkylthio, $C_1$–$C_2$-alkyl which is monosubstituted to pentasubstituted by identical or different substituents from the series consisting of fluorine and chlorine, by $C_1$–$C_4$-alkoxy which is monosubstituted to pentasubstituted by identical or different substituents from the series consisting of fluorine and chlorine, by $SCF_3$, $SCHF_2$, nitro, cyano, and phenyl which is optionally monosubstituted to tetrasubstituted by identical or different substituents from the series consisting of fluorine, chlorine, bromine, $C_1$–$C_3$-alkyl, $C_1$–$C_3$-alkoxy, $C_1$–$C_3$-alkylthio, $C_1$–$C_2$-alkyl which is monosubstituted to pentasubstituted by identical or different substituents from the series consisting of fluorine and chlorine, $C_1$–$C_4$-alkoxy which is monosubstituted to pentasubstituted by identical or different substituents from the series consisting of fluorine and chlorine, $SCF_3$ and $SCHF_2$.

D very particularly preferably represents 2-pyrrolyl or 3-pyrrolyl, each of which is optionally monosubstituted or disubstituted by identical or different substituents from the series consisting of fluorine, chlorine, $CH_3$ and $C_2H_5$, or represents phenyl which is substituted by CHO, cyano, carboxyl, di-$C_1$–$C_6$-alkoxy-$C_1$–$C_4$-alkyl or $C_1$–$C_6$-alkoxycarbonyl.

A particularly especially represents phenyl which is monosubstituted or disubstituted by identical or different substituents from the series consisting of fluorine and chlorine.

D particularly especially represents 2- or 3-pyrrolyl which is optionally monosubstituted or disubstituted by identical or different substituents from the series consisting of fluorine, chlorine, methyl and ethyl, or represents phenyl which is substituted by CHO, cyano, carboxyl, di-$C_1$–$C_6$-alkoxy-$C_1$–$C_4$-alkyl or $C_1$–$C_6$-alkoxycarbonyl.

The active compounds are suitable for combating animal pests, preferably arthropods and nematodes, particularly insects and arachnids, encountered in agriculture, in forests, in the protection of stored products and materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp..

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp.,

*Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds according to the invention are distinguished by a potent insecticidal and acaricidal activity.

They can be employed particularly successfully for combating plant-injurious insects, such as for example, against the larvae of the mustard beetle (*Phaedon cochleariae*) or against the larvae of the green rice leaf hopper (*Nephotettix cincticeps*) or against the caterpillars of the diamond-back moth (*Plutella maculipennis*).

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is, liquid solvents, and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

The active compound according to the invention can be present in its commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas, substances produced by microorganisms, and the like.

Examples of particularly advantageous components in the mixtures are the following:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cypro-conazole, cyprofuram, dichlorophene, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichiamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

Herbicides for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin;

nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuronethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

The active compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide ranges. The active compound concentration of the use forms can be from 0.0000001 to 95% by weight of active compound, preferably between 0.0001 and 1% by weight.

They are applied in the customary manner adapted to suit the use forms.

When used against hygiene pests and stored-product pests, the active compound is distinguished by outstanding residual action on wood and clay and by a good stability to alkali on lime substrate.

Preparation and use of the active compounds according to the invention can be seen from the examples which follow.

PREPARATION EXAMPLES

Example 1

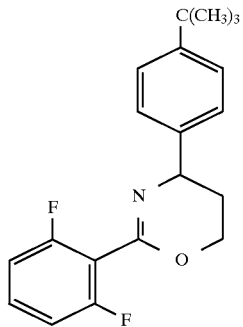
(I-1)

In an autoclave, a solution of 3 g (7.7 mmol) of N-[morpholin-4-yl-(4-tert-butylphenyl)-methyl]-2,6-difluorobenzamide (cf. Ex. IIa-1) in 20 ml of anhydrous dichloromethane and 25 ml (25 mmol) of titanium(IV) chloride (1-molar solution in dichloromethane) is saturated with dry hydrogen chloride gas at room temperature. Thereupon, ethylene is passed in at approximately 0° C. for approximately 20 to 30 minutes, and the mixture is subsequently stirred for 24 hours at 70° C. and an inherent pressure of approximately 14 bar. The reaction mixture is subsequently stirred with approximately 100 ml of ice-water, rendered alkaline at 0° C. using sodium hydroxide solution and extracted repeatedly using dichloromethane. The combined organic phases are dried over magnesium sulphate and concentrated. The oily residue is purified by chromatography.

0.83 g (32.5% of theory) of 4-(4-tert-butylphenyl)-2-(2,6-difluorophenyl)-5,6-dihydro-4H-1,3-oxazine is obtained.

$^1$H NMR (ppm in $CDCl_3$): 7.42–6.90 (m, 7H); 4.78 (m, 1H); 4.41–4,30 (m, 2H, 1H); 1.31 (s, 9H).

Example 2

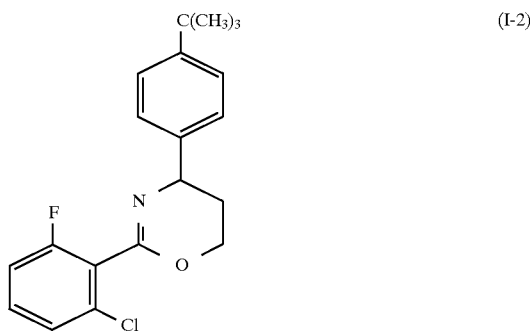
(I-2)

(without intermediate isolation of the compound (II))

3.5 g (20 mmol) of 2-chloro-6-fluorobenzamide are stirred with 3.4 g (21 mmol) of 4-tert-butylbenzaldehyde and 2.1 g (24 mmol) of morpholine for 18 hours at 50° C. in 40 ml of dichloromethane.

After cooling, the reaction mixture is treated with 45 ml of titanium(IV) chloride (1-molar solution in dichloromethane) and, in an autoclave, saturated with dry hydrogen chloride gas at room temperature. Thereupon, ethylene is passed in at approximately 0° C. for approximately 20 to 30 minutes, and the mixture is subsequently stirred for 24 hours at 70° C. at an inherent pressure of approximately 14 bar. The reaction mixture is stirred with approximately 150 ml of ice-water, rendered alkaline at 0° C. using sodium hydroxide solution and extracted repeatedly using dichloromethane. The combined organic phases are dried over magnesium sulphate and concentrated.

1.38 g (30% of theory) of 4-(4-tert-butylphenyl)-2-(2-chloro-6-fluorophenyl)-5,6-dihydro-4H-1,3-oxazine of a logP of 4.71 are obtained.

The following compound of the general formula (I) can be obtained in accordance with Examples 1 and 2 and analogously to the general process instructions:

TABLE 1
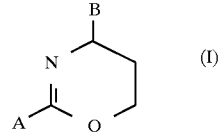
| Ex. No. | A | B |
|---|---|---|
| 3 | 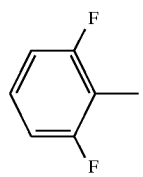 | 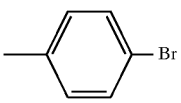 |
| 4 | 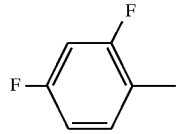 | 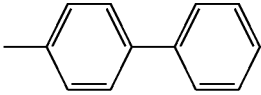 |
| 5 | 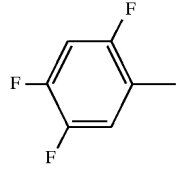 | 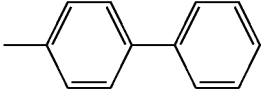 |
| 6 | 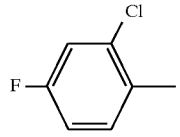 | 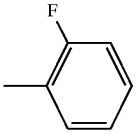 |
| 7 | 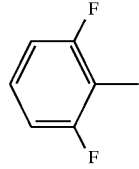 | 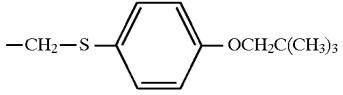 |
| 8 | 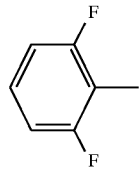 | 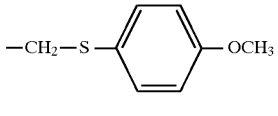 |
| 9 | 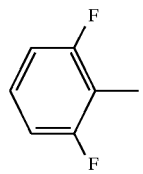 | 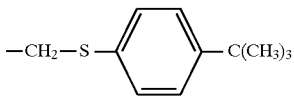 |
| 10 | 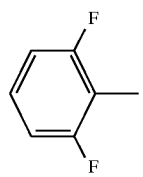 | 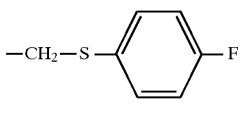 |

TABLE 1-continued $$\underset{A}{\overset{B}{\underset{O}{\bigwedge}}}\quad (I)$$

| Ex. No. | A | B |
|---|---|---|
| 11 | 2,6-difluorophenyl | $-CH_2-S-C_6H_4-SCH_2C(CH_3)_3$ (para) |
| 12 | 2,6-difluorophenyl | $-CH_2-C_6H_4-C_6H_4-Br$ (4,4'-biphenyl) |
| 13 | 2,6-difluorophenyl | $-CH_2-C_6H_4-OCH_3$ (para) |
| 14 | 2-chloro-6-fluorophenyl | $-CH_2-C_6H_4-OCH_3$ (para) |
| 15 | 2,6-difluorophenyl | $-CH_2-C_6H_4-C(CH_3)_3$ (para) |
| 16 | 2-fluoro-6-methoxyphenyl | $-CH_2-C_6H_4-C(CH_3)_3$ (para) |
| 17 | 2-fluorophenyl | $-CH_2-C_6H_4-OCH_3$ (para) |
| 18 | 2,6-difluorophenyl | $-CH_2-C_6H_4-OCF_3$ (para) |

TABLE 1-continued
$$\text{(I)}$$
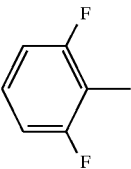
| Ex. No. | A | B |
|---|---|---|
| 19 | 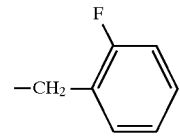 |  |
| 20 | 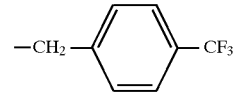 | 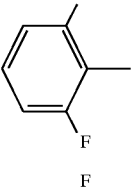 |
| 21 | 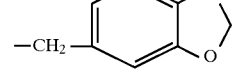 | 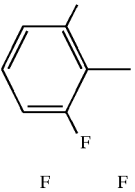 |
| 22 | 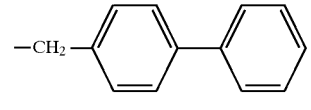 | 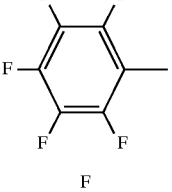 |
| 23 | 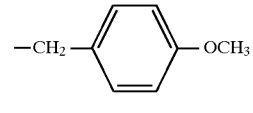 | 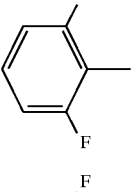 |
| 24 | 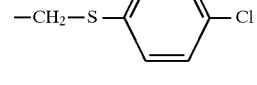 | 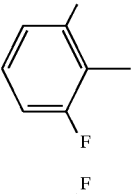 |
| 25 | 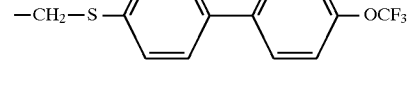 | 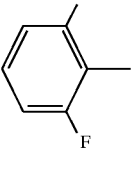 |
| 26 | 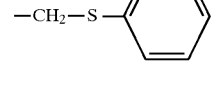 | |

TABLE 1-continued
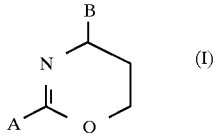
| Ex. No. | A | B |
|---|---|---|
| 27 | 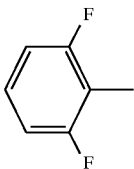 | —CH₂—S—⟨C₆H₄⟩—Br |
| 28 | 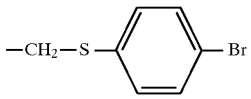 | —CH₂CH₂—⟨C₆H₅⟩ |
| 29 | 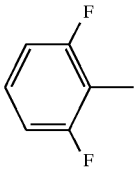 | —CH(CH₃)—O—⟨C₆H₄⟩—C(CH₃)₃ |
| 30 | 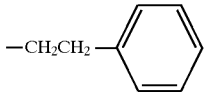 | —CH=CH—⟨C₆H₄⟩—C(CH₃)₃ |
| 31 | 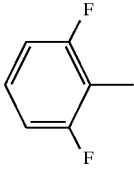 | —CH₂CH₂—⟨C₆H₄⟩—C(CH₃)₃ |
| 32 | 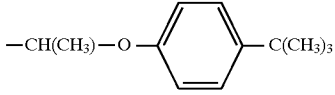 | —⟨C₆H₄⟩—⟨C₆H₅⟩ |
| 33 | 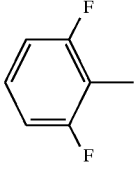 | —⟨C₆H₄⟩—OCH₂—⟨C₆H₅⟩ |

TABLE 2

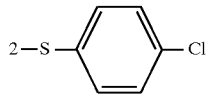

(Ia-1)

| Ex. No. | $Y_m$ | $X_n$ |
|---|---|---|
| 34 | 2,6-$F_2$ | 4-Cl |
| 35 | 2,6-$F_2$ | H |
| 36 | 2,6-$F_2$ | 4-$OCH_3$ |
| 37 | 2,6-$F_2$ | 4-O—CH—$(CH_3)_2$ |
| 38 | 2,6-$F_2$ | 4-O—$C_8H_{17}$(n) |
| 39 | 2,6-$F_2$ | 2-Cl |
| 40 | 2,6-$F_2$ | 3-Cl |
| 41 | 2,6-$F_2$ | 2,6-$Cl_2$ |
| 42 | 2,6-$F_2$ | 2,4-$Cl_2$ |
| 43 | 2,6-$F_2$ | 2,4,5-$Cl_3$ |
| 44 | 2-Cl, 6-F | H |
| 45 | 2-Cl, 6-F | 4-Cl |
| 46 | 2-Cl, 6-F | 4-$OCH_3$ |
| 47 | 2-Cl, 6-F | 4-O—CH—$(CH_3)_2$ |
| 48 | 2-Cl, 6-F | 4-O—$C_8H_{17}$(n) |
| 49 | 2-Cl, 6-F | 2-Cl |
| 50 | 2-Cl, 6-F | 3-Cl |
| 51 | 2-Cl, 6-F | 2,6-$Cl_2$ |
| 52 | 2-Cl, 6-F | 2,4-$Cl_2$ |
| 53 | 2-Cl, 6-F | 2,4,5-$Cl_3$ |
| 54 | 2,6-$F_2$ | 4-F |
| 55 | 2,6-$F_2$ | 2-F |
| 56 | 2,6-$F_2$ | 4-$C_3H_7$(n) |
| 57 | 2,6-$F_2$ | 4-$OCF_3$ |
| 58 | 2,6-$F_2$ | 4-$CF_3$ |
| 59 | 2,6-$F_2$ | 2-$CF_3$ |
| 60 | 2,6-$F_2$ | 2,4-$F_2$ |
| 61 | 2,6-$F_2$ | 2-Cl, 4-F |
| 62 | 2,6-$F_2$ | 2-Cl, 6-F |
| 63 | 2,6-$F_2$ | 2-OEt, 5-Br |
| 64 | 2,6-$F_2$ | 2-Cl, 4-OCH($CH_3)_2$ |
| 65 | 2-Cl, 6-F | 4-$CF_3$ |
| 66 | 2-Cl, 6-F | 2-Cl, 6-F |
| 67 | 2,6-$Cl_2$ | H |
| 68 | 2,6-$Cl_2$ | 4-Cl |
| 69 | 2,6-$Cl_2$ | 3-Cl |
| 70 | 2,6-$Cl_2$ | 2-Cl |
| 71 | 2,6-$Cl_2$ | 4-t-butyl |
| 72 | 2,6-$Cl_2$ | 4-$CF_3$ |
| 73 | 2-Cl | 2-Cl |
| 74 | 2,6-$F_2$ | 2-Br |
| 75 | 2,6-$F_2$ | 3-OPh |
| 76 | 2,6-$F_2$ | 4-OPh |
| 77 | 2,6-$F_2$ | 2-OPh |
| 78 | 2,6-$F_2$ | 4-N($CH_3)_2$ |
| 79 | 2,6-$F_2$ | 4-SPh |
| 80 | 2,6-$F_2$ | 2—S—⟨C6H4⟩—Cl |
| 81 | 2,6-$F_2$ | 2,3-$Cl_2$ |
| 82 | 2,6-$F_2$ | 3,4-$Cl_2$ |
| 83 | 2,6-$F_2$ | 3,5-$Cl_2$ |
| 84 | 2,6-$F_2$ | 2,5-$Cl_2$ |
| 85 | 2,6-$F_2$ | 2,6-$F_2$ |
| 86 | 2,6-$F_2$ | 2-F, 4-Cl |
| 87 | 2,6-$F_2$ | 2-Cl, 4-Br |
| 88 | 2,6-$F_2$ | 2-Br, 4-F |
| 89 | 2,6-$F_2$ | 2-Br, 6-F |
| 90 | 2,6-$F_2$ | 2-Br, 4-Cl |
| 91 | 2,6-$F_2$ | 2-Cl, 3-F |
| 92 | 2,6-$F_2$ | 2-Cl, 3-Br |
| 93 | 2,6-$F_2$ | 2-Cl, 3-$CH_3$ |
| 94 | 2,6-$F_2$ | 2-Cl, 4-OEt |
| 95 | 2,6-$F_2$ | 2-Cl, 4-$CH_3$ |
| 96 | 2,6-$F_2$ | 2-Cl, 3-OPh |
| 97 | 2,6-$F_2$ | 2-Cl, 3-t-butyl |
| 98 | 2,6-$F_2$ | 2-F, 3-Cl |
| 99 | 2,6-$F_2$ | 2-Br, 3-Cl |
| 100 | 2,6-$F_2$ | 3-Br, 4-Cl |
| 101 | 2,6-$F_2$ | 2-Cl, 4-$CF_3$ |
| 102 | 2,6-$F_2$ | 2-Cl, 4-t-butyl |
| 103 | 2,6-$F_2$ | 2-Cl, 4-$OCH_2CF_3$ |
| 104 | 2,6-$F_2$ | 2-Br, 4-OEt |
| 105 | 2,6-$F_2$ | 2-F, 4-t-butyl |
| 106 | 2,6-$F_2$ | 2,4-$(CH_3)_2$ |
| 107 | 2,6-$F_2$ | 2,3-$(CH_3)_2$ |
| 108 | 2,6-$F_2$ | 3-Br, 4-OEt |
| 109 | 2,6-$F_2$ | 2-OEt, 4-Cl |
| 110 | 2,6-$F_2$ | 2-OEt, 4-t-butyl |
| 111 | 2,6-$F_2$ | 2-OEt, 5-Cl |
| 112 | 2,6-$F_2$ | 2-OEt, 5-Br |
| 113 | 2,6-$F_2$ | 2-$OCH_2$—$C_2H_5$, 5-Br |
| 114 | 2,6-$F_2$ | 3,4-$(OEt)_2$ |
| 115 | 2,6-$F_2$ | 3-OEt, 4-t-butyl |
| 116 | 2,6-$F_2$ | 3-t-butyl, 4-OEt |
| 117 | 2,6-$F_2$ | 3-t-butyl, 4-O-n-Pr |
| 118 | 2,6-$F_2$ | 3-Cl, 5-$CF_3$, 2-O— (pyridine) |
| 119 | 2,6-$F_2$ | 4-Ph |
| 120 | 2,6-$F_2$ | 4-$OCH_2$Ph |
| 121 | 2,6-$F_2$ | 2,3-$Cl_2$, 4-$SCH_3$ |
| 122 | 2,6-$F_2$ | 2,3-$Cl_2$, 4-OEt |
| 123 | 2,6-$F_2$ | 2,3,4-$Cl_3$ |
| 124 | 2,6-$F_2$ | 2-OEt, 4,5-$Cl_2$ |
| 125 | 2,6-$F_2$ | 2-O-n-Pen., 4,5-$Cl_2$ |
| 126 | 2,6-$F_2$ | 2,4-$Cl_2$, 5-Br |
| 127 | 2,6-$F_2$ | 2-$OCH_3$, 4-Cl, 5-Br |
| 128 | 2,6-$F_2$ | 2-OEt, 4-Cl, 5-Br |
| 129 | 2,6-$F_2$ | 2-O-n-Pen., 4-Cl, 5-Br |
| 130 | 2,6-$F_2$ | 2,5-$(OCH_3)_2$, 4-t-butyl |
| 131 | 2,6-$F_2$ | 2,5-$Cl_2$, 4-OEt |
| 132 | 2,6-$F_2$ | 2,3,4,5,6-$F_5$ |
| 133 | 2-Cl, 6-F | 2,3-$Cl_2$ |
| 134 | 2-Cl, 6-F | 2,6-$F_2$ |
| 135 | 2-Cl, 6-F | 4-Br |
| 136 | 2-Cl, 6-F | 2,3,4-$Cl_2$ |
| 137 | 2-Cl, 6-F | 2-OEt, 3,4-$Cl_2$ |
| 138 | 2-Cl, 6-F | 2-O-n Pen., 4,5-$Cl_2$ |
| 139 | 2-Cl, 6-F | 2-OEt, 4-Cl, 5-Br |
| 140 | 2-Cl, 6-F | 2-O-n Pen., 4-Cl, 5-Br |

TABLE 2-continued

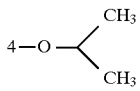
(Ia-1)

| Ex. No. | Y$_m$ | X$_n$ |
|---|---|---|
| 141 | 2,6-Cl$_2$ | 4—O—CH(CH$_3$)$_2$ |
| 142 | 2,6-Cl$_2$ | 4-OC$_8$H$_{17}$(n) |
| 143 | 2,6-Cl$_2$ | 2,3-Cl$_2$ |
| 144 | 2,6-Cl$_2$ | 2,4-Cl$_2$ |
| 145 | 2,6-Cl$_2$ | 2-O-nPr., 4-Cl, 5-Br |
| 146 | 2-Cl | 4-Cl |
| 147 | 2-F | 4-Cl |
| 148 | 2-CF$_3$ | 4-Cl |
| 149 | 2-CO$_2$CH$_3$ | 4-Cl |

TABLE 3

(Ia-2)

| Ex. No. | R$^a$ | R$^b$ | (R$^c$)$_q$ |
|---|---|---|---|
| 150 | H | F | H |
| 151 | H | Cl | H |
| 152 | F | F | H |
| 153 | Cl | F | H |
| 154 | Cl | Cl | H |
| 155 | H | Cl | 2-F |
| 156 | F | F | 2-F |
| 157 | Cl | F | 2-F |
| 158 | F | F | 3-F |
| 159 | Cl | F | 3-F |
| 160 | H | Cl | 4-F |
| 161 | F | F | 4-F |
| 162 | Cl | F | 4-F |
| 163 | F | F | 2-F, 4-F |
| 164 | Cl | F | 2-F, 4-F |
| 165 | F | F | 2-F, 4-Cl |
| 166 | F | F | 2-F, 4-(CH$_2$)$_4$CH$_3$ |
| 167 | F | F | 2-F, 4-(CH$_2$)$_5$CH$_3$ |
| 168 | F | F | 2-F, 4-(CH$_2$)$_6$CH$_3$ |
| 169 | F | F | 2-F, 4-(CH$_2$)$_7$CH$_3$ |
| 170 | Cl | F | 2-F, 4-(CH$_2$)$_7$CH$_3$ |
| 171 | Cl | F | 2-F, 4-OCH$_2$CH$_3$ |
| 172 | F | F | 2-F, 4-O(CH$_2$)$_3$CH$_3$ |

TABLE 3-continued (Ia-2)

| Ex. No. | R$^a$ | R$^b$ | (R$^c$)$_q$ |
|---|---|---|---|
| 173 | F | F | 2-F, 4-phenyl |
| 174 | F | F | 2-F, 4-(4-Cl-phenyl) |
| 175 | F | F | 2-F, 4-(4-CH$_2$CH$_3$-phenyl) |
| 176 | Cl | F | 2-F, 4-(4-CH$_2$CH$_3$-phenyl) |
| 177 | F | F | 2-F, 4-(4-CH$_2$CH$_2$CH$_3$-phenyl) |
| 178 | F | F | 2-F, 4-(4-CH(CH$_3$)$_2$-phenyl) |
| 179 | F | F | 2-F, 4-(4-OCF$_3$-phenyl) |
| 180 | Cl | F | 2-F, 4-(2-OCH$_2$CH$_3$, 5-F-phenyl) |
| 181 | F | F | 2-F, 4-(2-OCH$_2$CH$_3$, 5-C(CH$_3$)$_3$-phenyl) |
| 182 | F | F | 2-F, 5-F |
| 183 | F | F | 2-F, 5-Cl |
| 184 | F | F | 2-F, 6-F |
| 185 | F | F | 3-F, 4-F |
| 186 | F | F | 3-F, 4-Cl |
| 187 | Cl | F | 3-F, 4-Cl |
| 189 | F | F | 3-F, 4-(CH$_2$)$_5$CH$_3$ |
| 190 | F | F | 3-F, 4-OCH$_3$ |

TABLE 3-continued

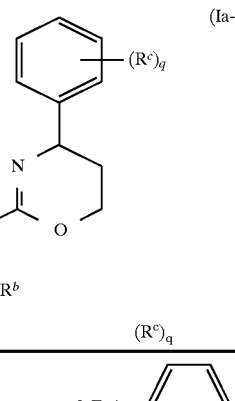
(Ia-2)

| Ex. No. | Rª | Rᵇ | (Rᶜ)q |
|---|---|---|---|
| 191 | Cl | F | 3-F, 4-phenyl |
| 192 | F | F | 3-F, 4-(4-CH₂CH₃-phenyl) |
| 193 | F | F | 3-F, 5-F |
| 194 | Cl | Cl | 3-F, 5-F |
| 195 | H | F | 2-Cl |
| 196 | F | F | 2-Cl |
| 197 | Cl | F | 2-Cl |
| 198 | F | F | 3-Cl |
| 199 | Cl | F | 3-Cl |
| 200 | H | Cl | 4-Cl |
| 201 | F | F | 4-Cl |
| 202 | Cl | F | 4-Cl |
| 203 | Cl | Cl | 4-Cl |
| 204 | F | F | 2-Cl, 3-Cl |
| 205 | Cl | F | 2-Cl, 3-Cl |
| 206 | F | F | 2-Cl, 4-F |
| 207 | H | Cl | 2-Cl, 4-Cl |
| 208 | F | F | 2-Cl, 4-Cl |
| 209 | Cl | F | 2-Cl, 4-Cl |
| 210 | F | F | 2-Cl, 4-CH₃ |
| 211 | F | F | 2-Cl, 4-CH₂CH₃ |
| 212 | F | F | 2-Cl, 4-CH₂CH₂CH₃ |
| 213 | F | F | 2-Cl, 4-(CH₂)₃CH₃ |
| 214 | F | F | 2-Cl, 4-CH₂CH(CH₃)₂ |
| 215 | F | F | 2-Cl, 4-C(CH₃)₃ |
| 216 | Cl | F | 2-Cl, 4-C(CH₃)₃ |
| 217 | F | F | 2-Cl, 4-(CH₂)₄CH₃ |
| 218 | F | F | 2-Cl, 4-(CH₂)₅CH₃ |
| 219 | F | F | 2-Cl, 4-(CH₂)₆CH₃ |
| 220 | F | F | 2-Cl, 4-(CH₂)₇CH₃ |
| 221 | Cl | F | 2-Cl, 4-(CH₂)₇CH₃ |
| 222 | F | F | 2-Cl, 4-(CH₂)₉CH₃ |
| 223 | F | F | 2-Cl, 4-(CH₂)₁₁CH₃ |
| 224 | F | F | 2-Cl, 4-OCH₂CH₂CH₃ |
| 225 | Cl | F | 2-Cl, 4-OCH₂CH₂CH₃ |
| 226 | F | F | 2-Cl, 4-O(CH₂)₄CH₃ |
| 227 | F | F | 2-Cl, 4-O(CH₂)₈CH₃ |
| 228 | F | F | 2-Cl, 4-phenyl |
| 229 | F | F | 2-Cl, 4-(4-F-phenyl) |
| 230 | F | F | 2-Cl, 4-(4-Cl-phenyl) |
| 231 | F | F | 2-Cl, 4-(4-CH₂CH₂CH₃-phenyl) |
| 232 | Cl | F | 2-Cl, 4-(4-CH₂CH₂CH₃-phenyl) |
| 233 | F | F | 2-Cl, 4-(4-CH(CH₃)₂-phenyl) |
| 234 | F | F | 2-Cl, 4-(4-C(CH₃)₃-phenyl) |
| 235 | F | F | 2-Cl, 4-(4-(CH₂)₇CH₃-phenyl) |
| 236 | F | F | 2-Cl, 4-(4-OCF₃-phenyl) |
| 237 | F | F | 2-Cl, 5-Cl |
| 238 | F | F | 2-Cl, 5-CF₃ |
| 239 | F | F | 3-Cl, 4-F |
| 240 | Cl | F | 3-Cl, 4-F |
| 241 | H | Cl | 3-Cl, 4-Cl |
| 242 | F | F | 3-Cl, 4-Cl |
| 243 | F | F | 3-Cl, 4-CH₃ |
| 244 | F | F | 3-Cl, 4-CH₂CH₂CH₃ |
| 245 | F | F | 3-Cl, 4-(CH₂)₅CH₃ |
| 246 | F | F | 3-Cl, 4-OCH₂CH₃ |
| 247 | F | F | 3-Cl, 4-(4-CH₃-phenyl) |
| 248 | F | F | 3-Cl, 4-(4-CH₂CH₂CH₃-phenyl) |
| 249 | Cl | F | 3-Cl, 4-(4-CH₂CH₂CH₃-phenyl) |

TABLE 3-continued (Ia-2)

| Ex. No. | Rᵃ | Rᵇ | (Rᶜ)_q |
|---|---|---|---|
| 250 | Cl | F | 3-Cl, 4-O-(4-Cl-phenyl) |
| 251 | F | F | 3-Cl, 5-Cl |
| 252 | H | F | 2-Br |
| 253 | F | F | 4-Br |
| 254 | Cl | F | 4-Br |
| 255 | F | F | 2-CH₃ |
| 256 | H | Cl | 3-CH₃ |
| 257 | F | F | 3-CH₃ |
| 258 | F | F | 4-CH₃ |
| 259 | F | F | 2-CH₃, 4-F |
| 260 | F | F | 2-CH₃, 4-Cl |
| 261 | Cl | Cl | 2-CH₃, 4-Cl |
| 262 | F | F | 2-CH₃, 4-(CH₂)₇CH₃ |
| 263 | F | F | 2-CH₃, 4-OCH₂CH₃ |
| 264 | Cl | F | 2-CH₃, 4-OCH₂CH₃ |
| 265 | F | F | 2-CH₃, 4-(4-Cl-phenyl) |
| 266 | F | F | 2-CH₃, 4-(4-CH₂CH₃-phenyl) |
| 267 | F | F | 2-CH₃, 4-(4-C(CH₃)₃-phenyl) |
| 268 | F | F | 2-CH₃, 4-(4-OCF₃-phenyl) |
| 269 | Cl | F | 2-CH₃, 4-(4-OCF₃-phenyl) |
| 270 | F | F | 2-CH₃, 4-O-(4-Cl-phenyl) |
| 271 | F | F | 2-CH₃, 4-O-(4-(CH₂)₅CH₃-phenyl) |
| 272 | F | F | 2-CH₃, 4-O-(4-CF₃-phenyl) |
| 273 | Cl | F | 2-CH₃, 4-O-(4-CF₃-phenyl) |
| 274 | F | F | 2-CH₃, 5-CH₃ |
| 275 | F | F | 2-CH₃, 5-CH(CH₃)₂ |
| 276 | Cl | Cl | 2-CH₃, 5-C(CH₃)₃ |
| 277 | F | F | 3-CH₃, 4-CH₃ |
| 278 | F | F | 3-CH₃, 4-(4-Cl-phenyl) |
| 279 | Cl | F | 3-CH₃, 4-O-(4-CH₃-phenyl) |
| 280 | F | F | 3-CH₃, 4-OCH₂-(4-CH₂CH₃-phenyl) |
| 281 | F | F | 2-CH₂CH₃ |
| 282 | F | F | 3-CH₂CH₃ |
| 283 | F | F | 4-CH₂CH₃ |
| 284 | F | F | 2-CH₂CH₃, 4-(4-Cl-phenyl) |
| 285 | F | F | 2-CH₂CH₃, 4-(4-CH₂CH₃-phenyl) |
| 286 | F | F | 2-CH₂CH₃, 4-(4-(CH₂)₃CH₃-phenyl) |
| 287 | F | F | 2-CH₂CH₃, 4-(4-OCF₃-phenyl) |
| 288 | Cl | F | 2-CH₂CH₃, 4-(2-Cl,4-Cl-phenyl) |

TABLE 3-continued

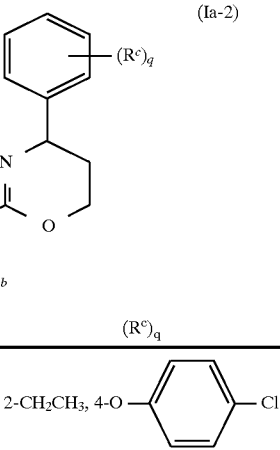
(Ia-2)

| Ex. No. | R$^a$ | R$^b$ | (R$^c$)$_q$ |
|---|---|---|---|
| 289 | F | F | 2-CH$_2$CH$_3$, 4-O—⟨C$_6$H$_4$⟩—Cl |
| 290 | F | F | 2-CH$_2$CH$_3$, 4-O—⟨C$_6$H$_4$⟩—OCF$_3$ |
| 291 | F | F | 2-CH$_2$CH$_3$, 5-Cl |
| 292 | F | F | 2-CH$_2$CH$_2$CH$_3$ |
| 293 | F | F | 3-CH$_2$CH$_2$CH$_3$ |
| 294 | F | F | 4-CH$_2$CH$_2$CH$_3$ |
| 295 | Cl | F | 4-CH$_2$CH$_2$CH$_3$ |
| 296 | F | F | 2-CH$_2$CH$_2$CH$_3$, 4-Cl |
| 297 | F | F | 3-CH(CH$_3$)$_2$ |
| 298 | F | F | 4-CH(CH$_3$)$_2$ |
| 299 | Cl | F | 4-CH(CH$_3$)$_2$ |
| 300 | F | F | 3-(CH$_2$)$_3$CH$_3$ |
| 301 | F | F | 4-(CH$_2$)$_3$CH$_3$ |
| 302 | F | F | 3-CH$_2$CH(CH$_3$)$_2$ |
| 303 | F | F | 4-CH$_2$CH(CH$_3$)$_2$ |
| 304 | F | F | 4-CH(CH$_3$)CH$_2$CH$_2$ |
| 305 | H | Cl | 3-C(CH$_3$)$_3$ |
| 306 | F | F | 3-C(CH$_3$)$_3$ |
| 307 | H | F | 4-C(CH$_3$)$_3$ |
| 308 | Cl | F | 4-C(CH$_3$)$_3$ |
| 309 | Cl | Cl | 4-C(CH$_3$)$_3$ |
| 310 | F | F | 3-(CH$_2$)$_4$CH$_3$ |
| 311 | F | F | 4-(CH$_2$)$_4$CH$_3$ |
| 312 | F | F | 3-(CH$_2$)$_2$CH(CH$_3$)$_2$ |
| 313 | F | F | 4-(CH$_2$)$_2$CH(CH$_3$)$_2$ |
| 314 | F | F | 3-C(CH$_3$)$_2$CH$_2$CH$_3$ |
| 315 | F | F | 4-C(CH$_3$)$_2$CH$_2$CH$_3$ |
| 316 | F | F | 3-CH$_2$C(CH$_3$)$_3$ |
| 317 | F | F | 4-CH$_2$C(CH$_3$)$_3$ |
| 318 | F | F | 3-(CH$_2$)$_5$CH$_3$ |
| 319 | Cl | F | 3-(CH$_2$)$_5$CH$_3$ |
| 320 | F | F | 4-(CH$_2$)$_5$CH$_3$ |
| 321 | F | F | 3-(CH$_2$)$_3$CH(CH$_3$)$_2$ |
| 322 | F | F | 4-(CH$_2$)$_3$CH(CH$_3$)$_2$ |
| 323 | F | F | 3-(CH$_2$)$_6$CH$_3$ |
| 324 | Cl | F | 3-(CH$_2$)$_6$CH$_3$ |
| 325 | F | F | 4-(CH$_2$)$_6$CH$_3$ |
| 326 | F | F | 3-(CH$_2$)$_7$CH$_3$ |
| 327 | F | F | 4-(CH$_2$)$_7$CH$_3$ |
| 328 | F | F | 3-(CH$_2$)$_8$CH$_3$ |
| 329 | Cl | Cl | 3-(CH$_2$)$_8$CH$_3$ |
| 330 | F | F | 4-(CH$_2$)$_8$CH$_3$ |
| 331 | F | F | 3-(CH$_2$)$_9$CH$_3$ |
| 332 | F | F | 3-(CH$_2$)$_{10}$CH$_3$ |
| 333 | F | F | 4-(CH$_2$)$_{11}$CH$_3$ |
| 334 | F | F | 4-(CH$_2$)$_{14}$CH$_3$ |
| 335 | F | F | 3-OCH$_3$ |
| 336 | Cl | F | 3-OCH$_3$ |
| 337 | F | F | 4-OCH$_3$ |
| 338 | F | F | 2-OCH$_3$, 4-C(CH$_3$)$_3$ |
| 339 | F | F | 2-OCH$_3$, 4-(CH$_2$)$_7$CH$_3$ |
| 340 | F | F | 2-OCH$_3$, 4-(CH$_2$)$_8$CH$_3$ |
| 341 | F | F | 2-OCH$_3$, 4-CF$_3$ |

TABLE 3-continued

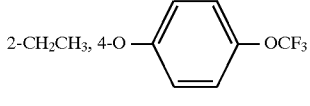
(Ia-2)

| Ex. No. | R$^a$ | R$^b$ | (R$^c$)$_q$ |
|---|---|---|---|
| 342 | F | F | 2-OCH$_3$, 4-⟨C$_6$H$_4$⟩—Cl |
| 343 | F | F | 2-OCH$_3$, 4-⟨C$_6$H$_4$⟩—CH$_2$CH$_2$CH$_3$ |
| 344 | F | F | 4-(CH$_2$)$_9$CH$_3$ |
| 345 | Cl | F | 2-OCH$_3$, 4-⟨C$_6$H$_4$⟩—CH$_2$CH$_2$CH$_3$ |
| 346 | F | F | 2-OCH$_3$, 4-⟨C$_6$H$_4$⟩—CH(CH$_3$)$_2$ |
| 347 | F | F | 2-OCH$_3$, 4-⟨C$_6$H$_4$⟩—C(CH$_3$)$_3$ |
| 348 | F | F | 2-OCH$_3$, 4-⟨C$_6$H$_4$⟩—OCF$_3$ |
| 349 | F | F | 2-OCH$_3$, 5-Cl |
| 350 | F | F | 2-OCH$_3$, 5-C(CH$_3$)$_3$ |
| 351 | F | F | 2-OCH$_3$, 5-(CH$_2$)$_6$CH$_3$ |
| 352 | F | F | 2-OCH$_2$CH$_3$ |
| 353 | Cl | F | 2-OCH$_2$CH$_3$ |
| 354 | F | F | 3-OCH$_2$CH$_3$ |
| 355 | F | F | 4-OCH$_2$CH$_3$ |
| 356 | F | F | 2-OCH$_2$CH$_3$, 4-F |
| 357 | H | Cl | 2-OCH$_2$CH$_3$, 4-Cl |
| 358 | F | F | 2-OCH$_2$CH$_3$, 4-Cl |
| 359 | F | F | 2-OCH$_2$CH$_3$, 4-CH$_3$, |
| 360 | F | F | 2-OCH$_2$CH$_3$, 4-CH(CH$_3$)$_2$ |
| 361 | F | F | 2-OCH$_2$CH$_3$, 4-C(CH$_3$)$_3$ |
| 362 | F | F | 2-OCH$_2$CH$_3$, 4-Si(CH$_3$)$_3$ |
| 363 | Cl | F | 2-OCH$_2$CH$_3$, 4-Si(CH$_3$)$_3$ |
| 364 | F | F | 2-OCH$_2$CH$_3$, 4-⟨C$_6$H$_4$⟩—Cl |
| 365 | F | F | 2-OCH$_2$CH$_3$, 4-⟨C$_6$H$_4$⟩—CH$_2$CH$_2$CH$_3$ |

TABLE 3-continued (Ia-2) structure: phenyl with $(R^c)_q$ substituent attached to a 6-membered ring containing N and O, fused to a phenyl ring bearing $R^a$ and $R^b$.

| Ex. No. | $R^a$ | $R^b$ | $(R^c)_q$ |
|---|---|---|---|
| 366 | Cl | F | 2-OCH$_2$CH$_3$, 4-(4-CH$_2$CH$_2$CH$_3$-phenyl) |
| 367 | F | F | 2-OCH$_2$CH$_3$, 4-(4-C(CH$_3$)$_3$-phenyl) |
| 368 | F | F | 2-OCH$_2$CH$_3$, 4-(4-OCF$_3$-phenyl) |
| 369 | Cl | F | 2-OCH$_2$CH$_3$, 4-(4-OCF$_3$-phenyl) |
| 370 | F | F | 2-OCH$_2$CH$_3$, 4-O-(4-OCF$_3$-phenyl) |
| 371 | F | F | 2-OCH$_2$CH$_3$, 5-Cl |
| 372 | F | F | 2-OCH$_2$CH$_3$, 5-Br |
| 373 | F | F | 2-OCH$_2$CH$_3$, 5-C(CH$_3$)$_3$ |
| 374 | F | F | 3-OCH$_2$CH$_2$CH$_3$ |
| 375 | F | F | 4-OCH$_2$CH$_2$CH$_3$ |
| 376 | F | F | 2-OCH$_2$CH$_2$CH$_3$, 4-F |
| 377 | Cl | F | 2-OCH$_2$CH$_2$CH$_3$, 4-F |
| 378 | F | F | 2-OCH$_2$CH$_2$CH$_3$, 4-Cl |
| 379 | F | F | 2-OCH$_2$CH$_2$CH$_3$, 4-CH$_3$ |
| 380 | F | F | 2-OCH$_2$CH$_2$CH$_3$, 4-CH(CH$_3$)$_2$ |
| 381 | F | F | 2-OCH$_2$CH$_2$CH$_3$, 5-(CH$_2$)$_6$CH$_3$ |
| 382 | F | F | 3-OCH(CH$_3$)$_2$ |
| 383 | F | F | 4-OCH(CH$_3$)$_2$ |
| 384 | Cl | F | 4-OCH(CH$_3$)$_2$ |
| 385 | F | F | 4-OCH$_2$CH(CH$_3$)$_2$ |
| 386 | F | F | 4-OCH(CH$_3$)CH$_2$CH$_3$ |
| 387 | F | F | 3-O(CH$_2$)$_4$CH$_3$ |
| 388 | F | F | 4-O(CH$_2$)$_4$CH$_3$ |
| 389 | F | F | 4-O(CH$_2$)$_2$CH(CH$_3$)$_2$ |
| 390 | F | F | 3-O(CH$_2$)$_5$CH$_3$ |
| 391 | F | F | 4-O(CH$_2$)$_5$CH$_3$ |
| 392 | Cl | F | 4-O(CH$_2$)$_5$CH$_3$ |
| 393 | F | F | 3-O(CH$_2$)$_6$CH$_3$ |
| 394 | F | F | 4-O(CH$_2$)$_6$CH$_3$ |
| 395 | F | F | 3-O(CH$_2$)$_7$CH$_3$ |
| 396 | F | F | 4-O(CH$_2$)$_7$CH$_3$ |
| 397 | Cl | F | 4-O(CH$_2$)$_7$CH$_3$ |
| 398 | F | F | 4-O(CH$_2$)$_8$CH$_3$ |
| 399 | F | F | 4-O(CH$_2$)$_9$CH$_3$ |
| 400 | F | F | 4-O(CH$_2$)$_{10}$CH$_3$ |
| 401 | F | F | 4-O(CH$_2$)$_{11}$CH$_3$ |
| 402 | F | F | 3-O(CH$_2$)$_{14}$CH$_3$ |
| 403 | F | F | 4-SCH$_3$ |
| 404 | F | F | 4-SCH(CH$_3$)$_2$ |
| 405 | F | F | 4-S(CH$_2$)$_8$CH$_3$ |
| 406 | F | F | 2-CF$_3$ |
| 407 | F | F | 3-CF$_3$ |
| 408 | Cl | F | 3-CF$_3$ |
| 409 | F | F | 4-CF$_3$ |
| 410 | F | F | 3-OCF$_3$ |
| 411 | F | F | 4-OCF$_3$ |
| 412 | F | F | 3-OCH$_2$CF$_3$ |
| 413 | Cl | F | 4-OCH$_2$CF$_3$ |
| 414 | F | F | 3-Si(CH$_3$)$_3$ |
| 415 | F | F | 4-Si(CH$_3$)$_3$ |
| 416 | Cl | F | 4-Si(CH$_3$)$_3$ |
| 417 | F | F | 4-Si(CH$_2$CH$_3$)$_3$ |
| 418 | Cl | F | 4-Si(CH$_2$CH$_3$)$_3$ |
| 419 | F | F | 4-Si[C(CH$_3$)$_3$, (CH$_3$)$_2$] |
| 420 | F | F | 4-cyclohexyl |
| 421 | Cl | F | 4-cyclohexyl |
| 422 | F | F | 4-(4-C(CH$_3$)$_3$-cyclohexyl) |
| 423 | Cl | F | 4-(4-C(CH$_3$)$_3$-cyclohexyl) |
| 424 | F | F | 4-phenyl |
| 425 | F | F | 4-(4-F-phenyl) |
| 426 | Cl | F | 4-(4-F-phenyl) |
| 427 | F | F | 4-(2-Cl-phenyl) |

TABLE 3-continued (Ia-2)

| Ex. No. | $R^a$ | $R^b$ | $(R^c)_q$ |
|---|---|---|---|
| 428 | F | F | 4-(3-Cl-phenyl) |
| 429 | F | F | 4-(4-Cl-phenyl) |
| 430 | F | F | 4-(4-CH₂CH₃-phenyl) |
| 431 | F | F | 4-(4-(CH₂)₃CH₃-phenyl) |
| 432 | F | F | 4-(4-CH(CH₃)CH₂CH₃-phenyl) |
| 433 | F | F | 4-(4-C(CH₃)₃-phenyl) |
| 434 | F | F | 4-(4-(CH₂)₄CH₃-phenyl) |
| 435 | F | F | 4-(4-OCH₃-phenyl) |
| 436 | F | F | 4-(4-OCH₂CH₃-phenyl) |
| 437 | F | F | 4-(4-OCH(CH₃)₂-phenyl) |
| 438 | F | F | 4-(4-CF₃-phenyl) |
| 439 | F | Cl | 4-(4-OCF₃-phenyl) |
| 440 | F | F | 4-(4-OCF₃-phenyl) |
| 441 | F | F | 4-(2-F,4-Br-phenyl) |
| 442 | Cl | F | 4-(2-F,4-Br-phenyl) |
| 443 | F | F | 4-(2-F,4-OCH₂CH₃-phenyl) |
| 444 | F | F | 4-(2,3-diCl-phenyl) |
| 445 | H | Cl | 4-(2,4-diCl-phenyl) |
| 446 | F | F | 4-(2,4-diCl-phenyl) |
| 447 | F | F | 4-(2-Cl,4-CH₃-phenyl) |

TABLE 3-continued (Ia-2)

| Ex. No. | R$^a$ | R$^b$ | (R$^c$)$_q$ |
|---|---|---|---|
| 448 | F | F | 4-Cl, OCF$_3$ |
| 449 | F | F | 2,4-diCl |
| 450 | F | F | 4-Br, OCF$_3$ |
| 451 | F | F | 4-CH$_3$, Cl |
| 452 | F | F | 2,4-di-CH$_3$ |
| 453 | F | F | 3,5-di-CH$_3$ |
| 454 | F | F | 4-OCH$_3$, C(CH$_3$)$_3$ |
| 455 | F | F | 4-OCH$_2$CH$_3$, C(CH$_3$)$_3$ |
| 456 | F | F | 2,4,5-tri-CH$_3$ |
| 457 | F | F | 4-(2,3,5,6-tetra-F) |
| 458 | Cl | F | 4-(2,3,5,6-tetra-F) |
| 459 | Cl | F | 3-, 4-O(CH$_2$)$_3$CH$_3$ |
| 460 | F | F | 4-CH$_2$-phenyl |
| 461 | F | F | 4-CH$_2$-(4-F-phenyl) |
| 462 | Cl | F | 4-CH$_2$-(4-F-phenyl) |
| 463 | F | F | 4-CH$_2$-(3-Cl-phenyl) |
| 464 | F | F | 4-CH$_2$-(4-Cl-phenyl) |

TABLE 3-continued (Ia-2)

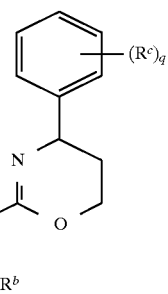

| Ex. No. | R$^a$ | R$^b$ | (R$^c$)$_q$ |
|---|---|---|---|
| 465 | F | F | 4-CH$_2$—C$_6$H$_4$—CH$_2$CH$_3$ |
| 466 | F | F | 4-CH$_2$—C$_6$H$_4$—CH$_2$CH$_2$CH$_3$ |
| 467 | F | F | 4-CH$_2$—C$_6$H$_4$—CH(CH$_3$)$_2$ |
| 468 | F | F | 4-CH$_2$—C$_6$H$_4$—(CH$_2$)$_3$CH$_3$ |
| 469 | Cl | F | 4-CH$_2$—C$_6$H$_4$—(CH$_2$)$_3$CH$_3$ |
| 470 | F | F | 4-CH$_2$—C$_6$H$_4$—C(CH$_3$)$_3$ |
| 471 | F | F | 4-CH$_2$—C$_6$H$_4$—(CH$_2$)$_5$CH$_3$ |
| 472 | F | F | 4-CH$_2$—C$_6$H$_4$—(CH$_2$)$_7$CH$_3$ |
| 473 | F | F | 4-CH$_2$—C$_6$H$_4$—OCH$_3$ |
| 474 | F | F | 4-CH$_2$—C$_6$H$_4$—OCF$_3$ |
| 475 | Cl | F | 4-CH$_2$—C$_6$H$_4$—OCF$_3$ |

TABLE 3-continued (Ia-2)

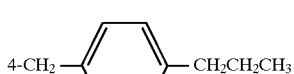

| Ex. No. | R$^a$ | R$^b$ | (R$^c$)$_q$ |
|---|---|---|---|
| 476 | F | F | 4-CH$_2$—(2,4-F$_2$-C$_6$H$_3$) |
| 477 | F | F | 4-CH$_2$—(2-Cl,4-F-C$_6$H$_3$) |
| 478 | F | F | 4-CH$_2$—(2,4-Cl$_2$-C$_6$H$_3$) |
| 479 | F | F | 4-CH$_2$—C$_6$F$_5$ |
| 480 | F | F | 4-CH$_2$CH$_2$—C$_6$H$_4$—Cl |
| 481 | F | F | 4-CH$_2$CH$_2$—C$_6$H$_4$—CH$_3$ |
| 482 | F | F | 4-CH$_2$CH$_2$—C$_6$H$_4$—CH$_2$CH$_2$CH$_3$ |
| 483 | F | F | 4-CH$_2$CH$_2$—C$_6$H$_4$—OCH$_3$ |
| 484 | F | F | 4-CH$_2$CH$_2$—(2,4-F$_2$-C$_6$H$_3$) |

TABLE 3-continued (Ia-2)

| Ex. No. | R$^a$ | R$^b$ | (R$^c$)$_q$ |
|---|---|---|---|
| 485 | F | F | 4-CH$_2$CH$_2$-(2,4-dichlorophenyl) |
| 486 | F | F | 4-CH$_2$CH$_2$CH$_2$-(4-fluorophenyl) |
| 487 | F | F | 4-CH$_2$CH$_2$CH$_2$-(4-chlorophenyl) |
| 488 | Cl | F | 4-CH$_2$CH$_2$CH$_2$-(4-chlorophenyl) |
| 489 | F | F | 4-OCH$_2$-phenyl |
| 490 | F | F | 4-OCH$_2$-(2-chlorophenyl) |
| 491 | F | F | 4-OCH$_2$-(4-CH(CH$_3$)$_3$-phenyl) |
| 492 | F | F | 4-OCH$_2$-(4-CH(CH$_3$)$_3$-phenyl) |
| 493 | F | F | 4-OCH$_2$-(2,6-difluorophenyl) |
| 494 | F | F | 3-O-phenyl |
| 495 | Cl | F | 3-O-phenyl |
| 496 | F | F | 4-O-phenyl |
| 497 | F | F | 4-O-(4-chlorophenyl) |
| 498 | F | F | 4-O-(4-bromophenyl) |
| 499 | F | F | 4-O-(4-CH$_3$-phenyl) |
| 500 | F | F | 4-O-(4-CH$_2$CH$_2$CH$_3$-phenyl) |
| 501 | F | F | 4-O-(4-CH(CH$_3$)CH$_2$CH$_3$-phenyl) |
| 502 | F | F | 4-O-(4-(CH$_2$)$_5$CH$_3$-phenyl) |
| 503 | F | F | 4-O-(4-OCH$_3$-phenyl) |
| 504 | F | F | 4-O-(3-CF$_3$-phenyl) |
| 505 | Cl | F | 4-O-(3-CF$_3$-phenyl) |

TABLE 3-continued

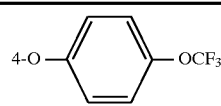
(Ia-2)

| Ex. No. | Rᵃ | Rᵇ | (Rᶜ)q |
|---|---|---|---|
| 506 | F | F | 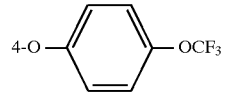 4-O—⟨⟩—OCF₃ |
| 507 | Cl | F | 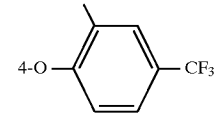 4-O—⟨⟩—OCF₃ |
| 508 | F | F | 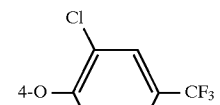 4-O—⟨Cl⟩—CF₃ |
| 519 | Cl | F | 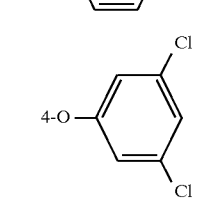 4-O—⟨Cl⟩—CF₃ |
| 510 | F | F | 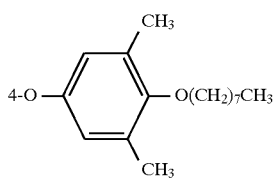 4-O—⟨Cl,Cl⟩ |
| 511 | F | F | 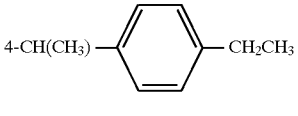 4-O—⟨CH₃,CH₃⟩—O(CH₂)₇CH₃ |
| 512 | F | F | 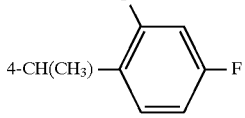 4-CH(CH₃)—⟨⟩—CH₂CH₃ |
| 513 | F | F | 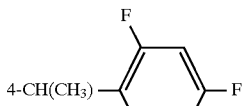 4-CH(CH₃)—⟨F⟩—F |
| 514 | Cl | F | 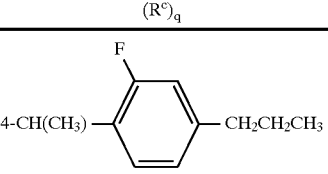 4-CH(CH₃)—⟨F⟩—F |
| 515 | F | F | 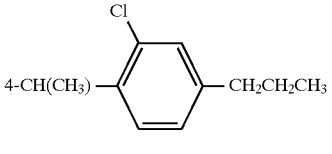 4-CH(CH₃)—⟨F⟩—CH₂CH₂CH₃ |
| 516 | F | F | 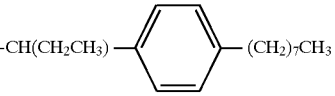 4-CH(CH₃)—⟨Cl⟩—CH₂CH₂CH₃ |
| 517 | F | F | 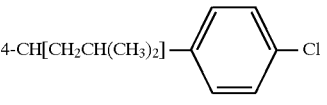 4-CH(CH₂CH₃)—⟨⟩—(CH₂)₇CH₃ |
| 518 | F | F |  4-CH[CH₂CH(CH₃)₂]—⟨⟩—Cl |
| 519 | F | F | 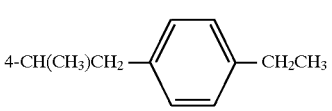 4-C(CH₃)₂—⟨⟩—OCH₂CH₃ |
| 520 | F | F | 4-CH(CH₃)CH₂—⟨⟩—CH₂CH₃ |
| 521 | F | F | —Si(CH₃)₂—⟨⟩ 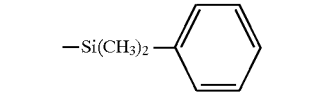 |
| 522 | Cl | F | 4-Si(CH₃)₂—⟨⟩ 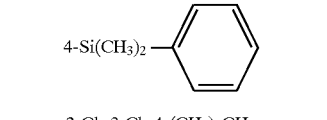 |
| 523 | F | F | 2-Cl, 3-Cl, 4-(CH₂)₄CH₃ |
| 524 | Cl | F | 2-Cl, 4-CH₃, 5-Br |
| 525 | F | F | 3-Cl, 4-OCH₂CH₃, 5-Cl |
| 526 | Cl | Cl | 3-Cl, 4-OCH₂CH₃, 5-Cl |
| 527 | Cl | F | 2-OCH₂CF₃, 4-Cl, 5-Cl |
| 528 | F | F | 2-OCH₂CH₃, 4-Cl, 5-Br |
| 539 | F | F | 2-OCH₂CH₂CH₃, 4-Cl, 5-Br |
| 530 | F | F | 2-OCH₂CH₂CH₃, 4-Cl, 5-CH₂CH₃ |
| 531 | Cl | F | 2-OCH₂CH₂CH₃, 4-Cl, 5-CH₂CH₃ |
| 532 | Cl | F | 3-CH₂CH₃, 4-Cl, 5-CH₂CH₃ |
| 533 | F | F | 2-OCH₃, 4-CH₃, 5-Cl |
| 534 | F | F | 2-OCH₂CH₃, 3-CH₃, 5-Cl |
| 535 | F | F | 2-CH₃, 4-CH₃, 5-CH₃ |
| 536 | F | F | 3-CH₃, 4-OCH(CH₃)₂, 5-CH₃ |
| 537 | F | F | 3-CH₃, 4-O(CH₂)₂CH(CH₃)₂, 5-CH₃ |
| 538 | Cl | F | 3-CH₃, 4-O(CH₂)₂CH(CH₃)₂, 5-CH₃ |

TABLE 3-continued

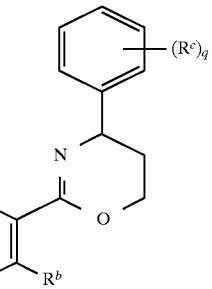
(Ia-2)

| Ex. No. | R$^a$ | R$^b$ | (R$^c$)$_q$ |
|---|---|---|---|
| 539 | F | F | 2-OCH$_3$, 3-C(CH$_3$)$_3$, 5-CH$_3$ |
| 540 | F | F | 2-CH$_3$, 3-CH$_3$, 4-CH$_3$, 5-CH$_3$ |
| 541 | F | F | 2-OCH$_3$, 3-CH(CH$_3$)$_2$, 5-CH$_2$CH$_3$ |
| 542 | Cl | F | 3-C(CH$_3$)$_3$, 4-OCH$_3$, 5-C(CH$_3$)$_3$ |
| 543 | F | F | 2-F, 4-(CH$_2$)$_6$CH$_3$, 6-F |
| 544 | F | F | 2-Cl, 3-F, 5-F |
| 545 | Cl | F | 2-Cl, 3-F, 5-F |
| 546 | H | F | 2-OCH$_2$CH$_2$CH$_3$, 4-F, 5-F |
| 547 | F | F | 2-OCH$_2$CH$_2$CH$_3$, 4-F, 5-F |
| 548 | Cl | F | 2-OCH$_2$CH$_2$CH$_3$, 4-F, 5-Br, 6-F |
| 549 | F | F | 2-F, 3-F, 4-O(CH$_2$)$_3$CH$_3$, 5-F, 6-F |
| 550 | F | F | 2-OCH$_2$CH$_3$, 3-C(CH$_3$)$_3$ |
| 551 | F | F | 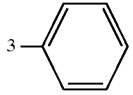 |
| 552 | Cl | F | 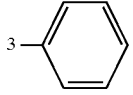 |
| 553 | F | F | 2-OCH$_2$CH$_2$CH$_3$, 3-Cl |
| 554 | Cl | F | 2-OCH$_2$CH$_2$CH$_3$, 3-Cl |

Example No. 555

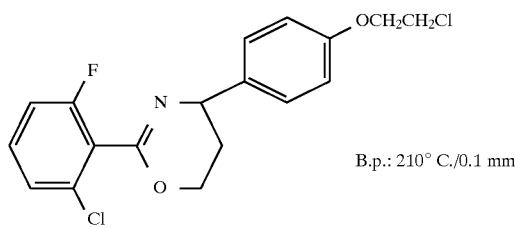

B.p.: 210° C./0.1 mm

The following abbreviations are used in the tables:

Me=methyl
Et=ethyl
Pr=propyl
Bu=butyl
Pen=pentyl
Ph=phenyl

TABLE 4

(Ib)

| Ex. No. | A | D | physical constant |
|---|---|---|---|
| Ib-1 | 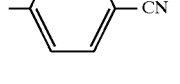 |  | |
| Ib-2 | 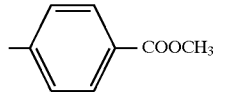 |  | |
| Ib-3 | 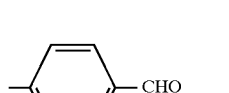 |  | |
| Ib-4 |  |  | $^1$HNMR (ppm in DMSO) 9.30 (br, OH) 4.66 (dd, CH) |
| Ib-5 | 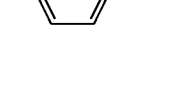 |  | $^1$HNMR (ppm in DMSO) 9.44 (br, OH) 4.68 (dd, CH) |

Preparation of the starting materials of the formula (IIa)

Example (IIa-1)

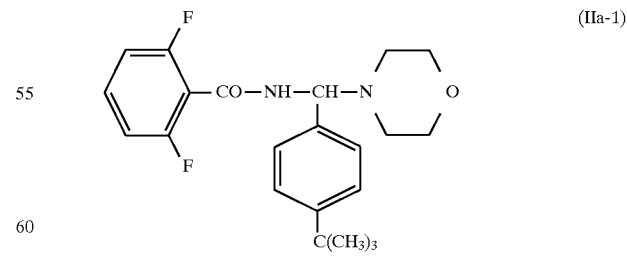
(IIa-1)

13.6 g (84 mmol) of 4-tert-butylbenzaldehyde and 8.5 (97.7 mmol) of morpholine are added to a solution of 12.8 g (81.5 mmol) of 2,6-difluorobenzamide in 100 ml of anhydrous methanol and the reaction mixture is stirred for 24 hours at approximately 40° to 50° C. It is subsequently stirred with approximately 100 ml of ice-water, and the precipitate is filtered off with suction, washed with water and dried.

21 g (67% of theory) of N-[morpholin-4-yl-(4-tert-butylphenyl)-methyl]-2,6-di-fluorobenzamide of melting point 199°–200° C. are obtained.

Example (IIa-2)

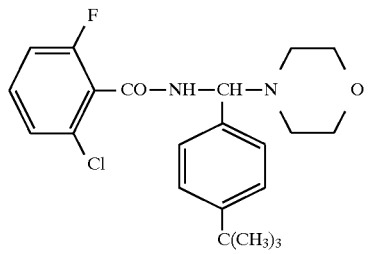

(IIa-2)

3.5 g (20 mmol) of 2-chloro-6-fluorobenzamide are stirred for 18 hours at 50° C. with 3.4 g (21 mmol) of 4-tert-butyl-benzaldehyde and 2.1 g (24.1 mmol) of morpholine in 30 ml of methanol. After cooling, the reaction mixture is stirred with 100 ml of ice-water, and the precipitate is filtered off with suction, washed with water and dried.

6.3 g (77.4% of theory) of N-[morpholin-4-yl-(4-tert-butylphenyl)-methyl]-2-chloro-6-fluoro-benzamide of melting point 180°–181° C. are obtained.

The following starting materials of the formula (IIa) are obtained in accordance with Examples (IIa-1) and (IIa-2) and analogously to the general preparation instructions:

TABLE A $$A-CO-NH-CH(B^2)-N(R^1)(R^2) \quad (IIa)$$

| Ex. No. | A | $B^2$ | $-N(R^1)(R^2)$ | M.p. (°C.) or $^1$H NMR |
|---|---|---|---|---|
| IIa-3 | 2,6-difluorophenyl | 4-bromophenyl | morpholin-4-yl | (ppm in CDCl$_3$) 6.44 (d, NH); 5.99 (d, CH) |
| IIa-4 | 2,6-difluorophenyl | 4-biphenylyl | morpholin-4-yl | (ppm in DMSO) 9.44 (d, NH); 5.97 (d, CH) |
| IIa-5 | 2,6-difluorophenyl | 4-(OCF$_3$)phenyl | morpholin-4-yl | 184–185 |
| IIa-6 | 2,6-difluorophenyl | $-C_3H_7$-i | morpholin-4-yl | 144 |

TABLE A-continued $$A-CO-NH-\overset{B^2}{\underset{|}{CH}}-N\overset{R^1}{\underset{R^2}{\diagdown}} \quad (IIa)$$

| Ex. No. | A | B² | $-N\overset{R^1}{\underset{R^2}{\diagdown}}$ | M.p. (°C.) or ¹H NMR |
|---|---|---|---|---|
| IIa-7 | 2,6-difluorophenyl | 4-C(CH₃)₃-phenyl | morpholino | 171 |
| IIa-8 | 2,6-difluorophenyl | 3-pyridyl | morpholino | 203–204 |
| IIa-9 | 2,6-difluorophenyl | 1-methyl-pyrrol-2-yl | morpholino | 187–188 |
| IIa-10 | 4-bromophenyl | 2,6-difluorophenyl | morpholino | 169–171 |
| IIa-11 | 2-fluoro-6-chlorophenyl | cyclohexyl | morpholino | 191–192 |
| IIa-12 | 2,6-difluorophenyl | cyclohexyl | morpholino | 185 |
| IIa-13 | 3-pyridyl | 4-C(CH₃)₃-phenyl | morpholino | 151 |
| IIa-14 | 2,6-difluorophenyl | 4-phenoxyphenyl | morpholino | 163 |

TABLE A-continued $$A-CO-NH-CH(B^2)-N(R^1)(R^2) \quad (IIa)$$

| Ex. No. | A | B² | −N(R¹)(R²) | M.p. (°C.) or ¹H NMR |
|---|---|---|---|---|
| IIa-15 | 2,6-diF-phenyl | −C₆H₄−O−CH₂−C₆H₅ | morpholino | 185 |
| IIa-16 | 2,6-diF-phenyl | −C₆H₄−COOCH₃ | morpholino | 180 |
| IIa-17 | 2,6-diF-phenyl | 3-HO-C₆H₄− | morpholino | 174–175 |
| IIa-18 | 2,6-diF-phenyl | 4-HO-C₆H₄− | morpholino | 177 |
| IIa-19 | 2,6-diF-phenyl | −C₆H₄−OCH₂−CH₂Cl | morpholino | 108 |
| IIa-20 | 2,6-diF-phenyl | −C₆H₄−CN | morpholino | 155–156 |
| IIa-21 | 2,6-diF-phenyl | C(CH₃)₃ | morpholino | 198 |

TABLE A-continued $$A-CO-NH-\underset{\underset{R^2}{|}}{CH}-\underset{\underset{R^2}{N}}{\overset{R^1}{\diagup}} \quad (IIa)$$

| Ex. No. | A | B² | $-N\diagup^{R^1}_{\diagdown R^2}$ | M.p. (°C.) or ¹H NMR |
|---|---|---|---|---|
| IIa-22 | 2,6-F₂-phenyl | 4-CH(OC₂H₅)₂-phenyl | morpholino | 96 |
| IIa-23 | 2,6-F₂-phenyl | 4-CHO-phenyl | morpholino | 55–56 |
| IIa-24 | 2,6-F₂-phenyl | 4-NHCOCH₃-phenyl | morpholino | 190 |
| IIa-25 | 2,6-F₂-phenyl | 2-thienyl | morpholino | 158 |
| IIa-26 | 2,6-F₂-phenyl | 4-I-phenyl | morpholino | 141 |

Use Examples

Example

Plutella test

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified period of time, the destruction in % is determined. 100% means that all the caterpillars have been killed; 0% means that none of the caterpillars have been killed.

In this test, a destruction of 100% was caused, after 7 days, by the compound of Example IIa-5 at an exemplary active compound concentration of 0.1%.

I claim:

1. Process for the preparation of compounds of the formula (I)

in which

A represents substituted phenyl, or represents in each case optionally substituted naphthyl, pyridyl, thienyl or pyrazolyl, and B represents hydrogen, alkyl, alkoxyalkyl, alkylthioalkyl, halogenoalkyl, alkenyl, optionally substituted cycloalkyl, or in each case optionally substituted phenyl, phenylalkyl, phenylalkenyl, phenoxyalkyl, phenylthioalkyl, pyridyl or 2- or 3-pyrrolyl characterized in that amide derivatives of the formula (II)

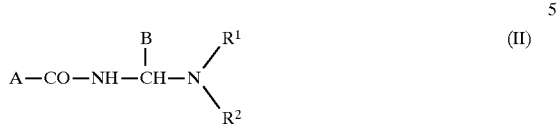

in which

A and B have the abovementioned meanings and

R$^1$ and R$^2$ are identical or different and in each case represent alkyl, or together with the N atom to which they are bonded represent an optionally substituted heterocycle are reacted with ethylene in the presence of hydrogen chloride gas and of a catalyst, if appropriate in the presence of a diluent.

* * * * *